US011041157B2

(12) United States Patent
Li et al.

(10) Patent No.: US 11,041,157 B2
(45) Date of Patent: *Jun. 22, 2021

(54) SLIT2D2-HSA FUSION PROTEIN AND USE THEREOF AGAINST TUMOURS

(71) Applicant: Huashun Li, Suzhou (CN)

(72) Inventors: Huashun Li, Suzhou (CN); Baoyong Ren, Suzhou (CN)

(73) Assignee: Huashun Li, Suzhou (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/573,596

(22) PCT Filed: Jun. 1, 2015

(86) PCT No.: PCT/CN2015/080523
§ 371 (c)(1),
(2) Date: Nov. 13, 2017

(87) PCT Pub. No.: WO2016/179861
PCT Pub. Date: Nov. 17, 2016

(65) Prior Publication Data
US 2018/0163214 A1    Jun. 14, 2018

(30) Foreign Application Priority Data

May 11, 2015 (CN) .......................... 201510236886.4

(51) Int. Cl.
| | | |
|---|---|---|
| *A61K 38/17* | (2006.01) | |
| *C07K 14/47* | (2006.01) | |
| *C07K 14/765* | (2006.01) | |
| *A61K 47/50* | (2017.01) | |
| *C12N 15/62* | (2006.01) | |
| *C12N 15/63* | (2006.01) | |
| *A61P 35/00* | (2006.01) | |
| *C07K 19/00* | (2006.01) | |
| *A61K 38/00* | (2006.01) | |

(52) U.S. Cl.
CPC .............. *C12N 15/625* (2013.01); *A61K 38/17* (2013.01); *A61K 47/50* (2017.08); *A61P 35/00* (2018.01); *C07K 14/47* (2013.01); *C07K 14/765* (2013.01); *C07K 19/00* (2013.01); *C12N 15/62* (2013.01); *C12N 15/63* (2013.01); *A61K 38/00* (2013.01)

(58) Field of Classification Search
CPC ........ A61K 38/17; A61K 47/50; C07K 14/47; C07K 14/765
See application file for complete search history.

(56) References Cited

U.S. PATENT DOCUMENTS

| | | | | |
|---|---|---|---|---|
| 7,507,413 B2* | 3/2009 | Rosen | ................... | C07K 14/765 424/192.1 |
| 2005/0054051 A1* | 3/2005 | Rosen | ................... | C07K 14/61 435/69.7 |
| 2014/0073565 A1* | 3/2014 | Kevil | ................. | G01N 33/5091 514/6.9 |

FOREIGN PATENT DOCUMENTS

CN        104119445 A       10/2014

OTHER PUBLICATIONS

Howitt et al., EMBO J., 2004, vol. 23(22):4406-4412.*
Wang et al., Cell, 1999, vol. 96:771-784.*
Morlot et al., PNAS, 2007, vol. 104(38):14923-14928.*
Biao Wang et al., "Induction of tumor angiogenesis by Slit-Robo signaling and inhibition of cancer growth by blocking Robo activity", Cancer Cell, Jul. 2003, vol. 4, pp. 19-29.
Li-Jing Wang et al., "Targeting Slit—Roundabout signaling inhibits tumor angiogenesis in chemical-induced squamous cell carcinogenesis", Cancel Sci., Mar. 2008, vol. 99, No. 3, pp. 510-517.
Cecile Morlot et al., "Production of Slit2 LRR domains in mammalian cells for structural studies and the structure of human Slit2 domain 3", Acta Crystallographica Section D Biological Crystallography, 2007, 63, pp. 961-968.
Elena Seiradake et al., "Structure and functional relevance of the Slit2 homodimerization domain", European Molecular Biology Organization reports, vol. 10, No. 7, 2009, pp. 736-741.
Cecile Morlot et al., "Structural insights into the Slit-Robo complex", Proceedings of the National Academy of Sciences of the United States of America, vol. 104, No. 38, Sep. 18, 2007, pp. 14923-14928.

* cited by examiner

*Primary Examiner* — Xiaozhen Xie
(74) *Attorney, Agent, or Firm* — Novick, Kim and Lee, PLLC; Bin Lu; Zhi Yang Xue

(57) ABSTRACT

Provided in the present invention are a Slit2D2-HAS fusion protein and the use thereof against tumours. The fusion protein can significantly inhibit the migration of tumour cells. Also provided in the present invention are a pharmaceutical composition comprising the fusion protein and a method for preparing the fusion protein.

5 Claims, 16 Drawing Sheets

Specification includes a Sequence Listing.

| Group | statistics for the number of animals | number of metastasis animals | degree of lymphatic metastasis (>10%) | metastasis positive rate (%) | degree of lymphatic metastasis (>10%) rate |
|---|---|---|---|---|---|
| Vehicle | 10 | 9 | 5 | 90.0% | 50% |
| Slit2D2-HSA 10mg/kg | 9 | 7 | 4 | 77.8% | 44% |
| Slit2D2-HSA 5mg/kg | 9 | 6 | 2 | 66.7% | 22% |

SLIT2D2-HSA FUSION PROTEIN AND USE THEREOF AGAINST TUMOURS

TECHNICAL FIELD

The present invention relates to biomedical fields, in particular, the present invention relates to the preparation of recombinant protein Slit2D2-HSA and the application thereof as anti-tumor drug in antitumor.

BACKGROUND ART

Tumor is a disease caused by the abnormal growth of the body cells, the proliferation of the tumor cells can not be controlled, and the metastasis and infiltration into the surroundings or the infiltration into the distal tissues through the blood circulation can lead to the malignant transformation of the body and endanger the life. Such diseases can greatly endanger human life and health, but the treatment method is still very limited. For the treatment of cancer, although there has been some progress in the past two decades, effective drugs are still limited and there is an urgent need for innovative thinking to develop new drugs. The key steps in the development and progression of oncological diseases involve cell migration, infiltration and distant metastasis, a new generation of anticancer drugs can be developed based on this feature. Studies for the neural guidance factor over the past two decades have found many important protein factors and revealed new cellular physiological mechanism. The representative factor Slit is a trend factor for neural axon guidance and neuronal migration. In recent years, Slit and the receptor Robo thereof have been found to regulate the migration of tumor cells, the migration of inflammatory cells and the migration of vascular endothelial cells, which are closely related to the development of tumor cells and inflammatory diseases.

Although the Slit/Robo signaling pathway has the potential for the development of oncology drug. However, there are four problems for the direct use of slit2 protein in drug development. Firstly, slit2 has a molecular weight of nearly 200 kd which is a large molecular weight and can affect drug absorption in vivo. Secondly, Slit2 itself has a relatively short half-life in vivo. Thirdly, there is opposite conclusion to tumor metastasis on Slit2, indicating that Slit2 can promote tumor metastasis (Wang, Xiao et al. 2003, Wang, Zhao et al. 2008). Fourthly, Slit2 can affect angiogenesis in vivo, slit2 itself can promote vascular endothelial cell migration and angiogenesis. However, the VEGF-induced vascular endothelial cell migration and angiogenesis can be inhibited by Slit2 under the action of VEGF cytokines. The drug development of Slit2 will affect the cardiovascular system in vivo, and result in adverse reactions.

SUMMARY OF THE INVENTION

The purpose of the present invention is to provide a fusion protein and the use thereof in anti-tumors.

In the first aspect of the present invention, a fusion protein is provided, and the fusion protein has a structure as shown in formula Ia or formula Ib:

C-A-B (Ia), or

C—B-A (Ib)

wherein,
A is a protein element comprising the second domain D2 of Slit2 and the element A is 200-300 amino acids in length;

B is a HSA protein element;
C is an optional signal peptide sequence;
"-" represents a peptide bond or a peptide linker connecting each element above mentioned.

In another preferred embodiment, the element A has an amino acid sequence as shown in SEQ ID NO.: 1 and has 207-250 amino acids in length.

In another preferred embodiment, the element A has a sequence as shown in SEQ ID NO.: 1.

In another preferred embodiment, the element B has a sequence as shown in SEQ ID NO.: 2.

In another preferred embodiment, the D2 has a flanking sequence, which comprises:
a first flanking sequence at the amino terminus of D2; and/or
a second flanking sequence at the carboxyl terminal of D2.

In another preferred embodiment, the first flanking sequence is consisted of 1-5 amino acid residues.

In another preferred embodiment, the second flanking sequence is consisted of 1-2 amino acid residues.

In another preferred embodiment, the first and second flanking sequence are derived from amino acid sequences at two flanks of the second domain D2 (SEQ ID NO.: 1) of the native Slit2 protein, respectively.

In another preferred embodiment, the element A is derived from a slit2 protein in mammals (such as humans).

In another preferred embodiment, the element B is derived from a HSA protein in mammals (such as humans).

In another preferred embodiment, the length of the peptide linker is 0-10 amino acids, preferably, 1-5 amino acids.

In another preferred embodiment, the fusion protein further comprises a signal peptide element C.

In another preferred embodiment, the fusion protein does not contain a signal peptide, and the structure is shown as follows A-B (IIa), or B-A (IIb)

wherein A, B and "-" are defined above.

In another preferred embodiment, the fusion protein is selected from the group consisting of:

(A) a polypeptide having an amino acid sequence as shown in SEQ ID NO.: 3;

(B) a polypeptide having an amino acid sequence having ≥80% homology to the amino acid sequence of SEQ ID NO.: 3 (preferably, ≥90% homology; more preferably, ≥95% homology; most preferably, ≥97% homology, such as ≥98% homology, ≥99% homology), and the polypeptide has the tumor inhibitory activity;

(C) a derivative polypeptide which is formed from any one of the amino acid sequences of SEQ ID NO.: 3 by substitution, deletion, or addition of 1-5 amino acids and retains the tumor inhibitory activity.

In another preferred embodiment, the amino acid sequence of the fusion protein is shown in SEQ ID NO.: 3.

In another preferred embodiment, the fusion protein has one or more characteristics selected from the group consisting of:

a) an activity of inhibiting tumor cell migration;
b) an activity of inhibiting HUVEC migration;
c) an activity of inhibiting tumor cell invasion, and
d) an activity of inhibiting tumor growth.

In the second aspect, an isolated polynucleotide is provided, and the polynucleotide encodes the fusion protein according to the first aspect of the present invention.

In the third aspect, a vector is provided, which comprises the polynucleotide according to the second aspect of the present invention.

In the fourth aspect, a host cell is provided, which comprises the vector according to the third aspect of the present invention or the genome thereof is integrated with the polynucleotide according to the second aspect of the present invention.

In another preferred embodiment, the host cell is a prokaryotic cell or an eukaryotic cell (such as a CHO cell, an NSO cell, or a 293 cell).

In the fifth aspect, a method for producing a protein is provided, which comprises the following steps:

culturing the host cell according to the fourth aspect of the present invention under a condition suitable for expressing, thereby expressing the fusion protein according to the first aspect of the present invention; and isolating the fusion protein.

In the sixth aspect, a pharmaceutical composition is provided, which comprises:

the fusion protein according to the first aspect of the present invention, and a pharmaceutically acceptable carrier.

In the seventh aspect, a use of the fusion protein according to the first aspect of the present invention is provided, for the manufacture of a medicament for the treatment or prevention of tumors.

In another preferred embodiment, the tumor is selected from the group consisting of: breast cancer, lung cancer, colorectal cancer, pancreatic cancer, ovarian cancer, prostatic cancer, renal carcinoma, liver cancer, cerebral cancer, melanoma, multiple myeloma, chronic myeloid leukemia, blood cancers, and lymphoma.

In the tenth aspect, a method for treating a tumor is provided, which comprises a step of:

administering the fusion protein according to the first aspect of the present invention to a subject in need.

In another preferred embodiment, the fusion protein is administered as a monomer and/or dimer.

In another preferred embodiment, the subject is a human.

It should be understood that within the scope of the present invention, any of the technical features specifically described above and below (such as the Examples) can be combined with other technical features, thereby constituting a new or preferred technical solution which needs not be described one by one.

BRIEF DESCRIPTION OF DRAWINGS

FIG. 14A shows the tumor volume of mice in different experiment groups, revealing that the tumor volume of the fusion protein experiment group is significantly smaller than that in the vehicle control group. FIG. 14B shows the growth curve of the tumor, indicating that the tumor growth rate in the experiment group of the fusion protein is significantly lower than that in the vehicle control group. FIG. 14C shows how body weight of the mice changes after inoculation of the tumor in each experiment group. No significant difference between the control group and experiment group indicates that the fusion protein of the present invention has no obvious side effects. FIG. 14D shows inhibitory effect of the drug on tumor cell metastasis in the metastasis evaluation model established by surgical excision of the tumor after each experiment group is inoculated with tumor cells and grew to a certain stage. The results show that the fusion protein of the present invention has a significant inhibitory effect on MDA-MB-231 cells in lung metastasis and lymph node metastasis of mice. FIG. 14E shows H&E staining for the tumor lung metastasis. FIG. 14F shows H&E staining for the tumor lymph node metastasis.

DETAILED DESCRIPTION OF INVENTION

Figure 2:
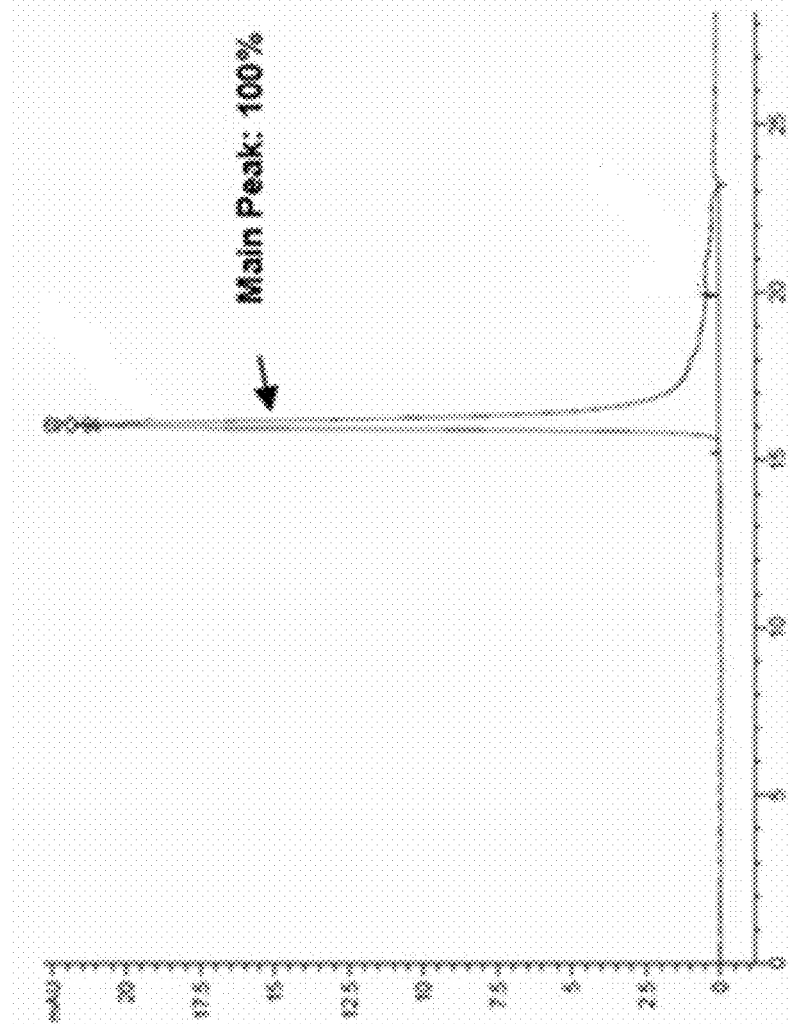
FIG. 2 shows a HPLC detection result after purification of the SlitD2-HSA fusion protein.

After extensive and intensive researches, the inventors of the invention have obtained a SlitD2-HAS fusion protein, and the experimental results show that the fusion protein can significantly inhibit tumor cell migration. Furthermore, the prior art shows that Slit2 has a dual effect of the promotion and inhibition on different tumors. However, the inventors have unexpectedly found that the fusion protein of the present invention shows an inhibitory effect on different tumors. Based on this, the invention was completed.

Before describing the present invention, it should be understood that the invention is not limited to the described particular methodology and experimental conditions, as such methods and conditions may be varied. It is also to be understood that the terminology used herein is only for the purpose of describing particular embodiments, and is not intended to be limiting, and the scope of the invention will be limited only by the appended claims.

Unless otherwise defined, all technical and scientific terms used herein have the same meaning as commonly understood by the ordinary skilled in the art to which this invention belongs. As used herein, the term "about" when used in reference to a particular listed value means that the value can vary from the listed value by no more than 1%. For example, as used herein, the expression of "about 100" includes all values between 99 and 101 (for example, 99.1, 99.2, 99.3, 99.4, etc.).

Although any methods and materials similar or equivalent to those described in this disclosure may be used in the practice or testing of the present invention, the preferred methods and materials are exemplified herein.

Slit Protein

Slit is a class of secreted glycoprotein with a molecular weight of about 200 kD. There are three Slit genes cloned in mammals, which are named Slit1, Slit2 and Slit3, respectively. Its structure consists of the N-terminal signal peptide, four leucine-rich repeats (LRRs) and multiple EGF-like repeats (7 repeats in *drosophila* and 9 repeats in vertebrates). Studies have shown that the LRRs is a binding domain of the Slit protein and the receptor Robo. Slit protein plays a role by binding to the receptor Robo. Robo is a transmembrane receptor protein, and four Robo genes have been cloned in mammals. From the perspective of species evolution, the extracellular portions of Robo 1, 2, and 3 are very conservative and consist of five Ig-like functional regions and three Fibronectin type III repeats from *drosophila* to humans. Robos have a very short transmembrane region and a longer intracellular region. According to the conservatism of sequence, the intracellular domain is divided into four smaller regions, named CC0, CC1, CC2 and CC3, respectively. The structure of Robo 4 is very different from that of the other three family members. The extracellular domain has only two Ig-like functional regions and three Fibronectin type III repeats; and the intracellular domain has only two regions of CC0 and CC2. The extracellular IgG domain of Robos is thought to be required for binding to the ligand Slit, while the longer intracellular domain interacts with some important signaling molecules and participates in the downstream signal transduction of Slit/Robo to complete the delivery of the stimulation signal from the outside of the cell to the internal skeleton. Analysis of the protein structure of interacting region between slit2 and Robo have found that the second domain D2 of slit2 binds to Ig1 of Robo1 and initiates signal transduction (Morlot, Hemrika et al. 2007, Hohenester 2008, Seiradake, von Philipsborn et al. 2009).

In recent years, the effect of the reaction axis SDF-1/CXCR4 formed by the interaction of CXC chemokinereceptor-4 (CXCR4) and its ligand stromal cell derived factor-1 (SDF-I) on tumor invasion and metastasis is attracting more and more attention. The combination of chemokine CXCL12 and CXCR4 can lead to the actin polymerization and the formation of cellular pseudopod, which can cause cancer cells to break through the basement membrane and invade and promote the movement and distant metastasis of cancer cells, resulting in chemotactic movement and invasive response. This series of effects is positively correlated with the dose of SDF-1 and SDF-1 has been shown to be involved in local invasion and organ-specific metastasis of breast cancer, prostate cancer, liver cancer, non-small cell lung cancer, fibrosarcoma, ovarian cancer, medulloblastoma, pancreatic cancer, colon cancer, melanoma and other cancer.

It has also been found that ROBO1 is expressed in 45% of breast cancer DU4475 cells and ROBO2 is expressed in 20% of breast cancer DU4475 cells; ROBO1 is expressed in 35% of MDA-MB-231 cells and ROBO4 is expressed in 21% of MDA-MB-231 cells. SDF-1 can induce the migration and invasion of breast cancer cell through the CXCR4/CXCL12 signaling pathway, but this process can be inhibited by slit2 and the cell adhesion behavior thereof can also be inhibited. Other studies have also demonstrated that Slit2 (30 pM or 100 pM) can effectively inhibit tumor migration induced by SDF-1 (10 nM).

Fusion Protein and the Preparation Thereof

In the present invention, "fusion protein", "recombinant protein", "the protein of the present invention", "the fusion protein of the present invention" are used interchangeably, and refer to a structure of Formula Ia or Formula Ib, that is, a fusion protein containing a protein element including Slit2D2 and a HSA protein element. A representative example is Slit2D2-HAS. The protein of the present invention can be a monomer or a multimer (such as a dimer) formed from a monomer. In addition, it should be understood that the term also includes the active fragments and derivatives of the fusion protein.

As used herein, "isolated" refers to the material is isolated from its original environment (if it is a natural substance, the original environment is the natural environment). Such as, the polynucleotides and polypeptides in the native state of the living cells are not isolated and purified, but the same polynucleotides or polypeptides are isolated from other substances present in the natural state, then they are isolated and purified.

As used herein, "isolated fusion protein" refers to the fusion protein is basically free of other proteins, lipids, carbohydrates or other substances that are naturally associated with it. The skilled in the art can purify the fusion protein using standard protein purification techniques. Substantially pure protein can produce a single primary band on non-reductive polyacrylamide gels.

The polynucleotides of the present invention can be in the form of DNA or RNA. DNA includes cDNA, genomic DNA, or synthetic DNA. DNA may be single-stranded or double-stranded. DNA may be a coding strand or non-coding strand.

The present invention also relates to variants of the polynucleotides as described above, which encode fragments, analogs and derivatives of proteins having the same amino acid sequence as the present invention. Variants of such polynucleotides may be naturally occurring allelic variants or non-naturally occurring variants. Such nucleotide variants include substitution variants, deletion variants, and insertion variants. As is known in the art, an allelic variant is an alternative form of a polynucleotide, which may be a substitution, deletion or insertion of one or more nucleotides, but its function of encoding polypeptide will not be substantially altered.

As used herein, the term "primer" refers to a generic term for oligonucleotides that pair with a template from which a DNA polymerase can act to synthesize a DNA complementary to the template. Primers can be a native RNA, DNA, or any form of natural nucleotide. Primers can even be non-natural nucleotides such as LNA or ZNA and the like. Primers are "substantially" (or "essentially") complementary to a particular sequence on a strand of the template. Primers must be sufficiently complementary to one strand in the template to begin the extension, but the primer sequence need not be completely complementary to the template sequence. For example, a sequence not complementary to the template is added to the 5' end of a primer, 3' end of which is complementary to the template, the primer can still be substantially complementary to the template. As long as sufficient length of primer can be completely bound to the template, non-fully complementary primers can also form a primer-template complex with the template for amplification.

A nucleotide full length sequence or fragment thereof of the fusion protein or the element thereof (such as Slit2D2) of the present invention can generally be obtained by a PCR amplification method, a recombinant method or an artificial synthetic method. For a PCR amplification method, primers can be designed according to the relevant nucleotide sequences has been disclosed, particularly the open reading frame sequences, and the commercially available cDNA libraries or cDNA libraries prepared by the conventional methods known to the skilled in the art can be used as a template, and the relevant sequences were obtained by amplification. When the sequence is longer, two or more PCR amplifications are usually needed, and then each of the amplified fragments are spliced together in the correct order.

Once the relevant sequence is obtained, the relevant sequence can be obtained in bulk using a recombination method. This is usually done by cloning it into a vector, then transferring it into a cell, and then isolating the relevant sequence from the proliferating host cells by the conventional method.

In addition, the relevant sequence can also be synthesized using artificial synthesis methods, particularly when the fragment is shorter. In general, a very long fragment can be obtained by firstly synthesizing multiple small fragments and then ligating them.

The method of amplifying DNA/RNA using PCR technique is preferably used to obtain the gene of the present invention. Primers for PCR can be appropriately selected according to the sequence information of the present invention disclosed herein and can be synthesized by conventional methods. The amplified DNA/RNA fragments can be isolated and purified by conventional means, such as by gel electrophoresis.

The present invention also relates to a vector containing the polynucleotide of the present invention, and a host cell produced by genetic engineering using the vector or a fusion protein encoding sequence of the present invention, and a method for producing the protein of the present invention by recombinant techniques.

With the conventional recombinant DNA technique, the polynucleotide of the present invention can be used to express or produce the recombinant protein. Generally, the method comprises the following steps:

(1) Transforming or transducing a suitable host cell with the polynucleotide (or variant thereof) of the present invention encoding the protein of the present invention or a recombinant expression vector containing said polynucleotide;

(2) Culturing the host cell in a suitable culture medium;

(3) Isolating and purifying protein from the culture medium or cell.

An expression vector containing an encoding DNA sequence of the protein of the present and a suitable transcription/translation control signal can be constructed by the methods well known to the skilled in the art. These methods include recombinant DNA technology in vitro, DNA synthesis technology, recombination techniques in vivo and the like. The DNA sequence can be effectively linked to a suitable promoter in the expression vector to direct mRNA synthesis. The expression vector also includes a ribosome binding site for translation initiation and a transcription terminator.

In addition, the expression vector preferably comprises one or more selectable marker genes to provide the selection of phenotypic traits for the transformed host cells, such as dihydrofolate reductase, neomycin resistance, and green fluorescent protein (GFP) for eukaryotic cell culture, or tetracycline or ampicillin resistance for *E. coli*.

A vector comprising an appropriate DNA sequence and a suitable promoter or a control sequence as described above can be used to transform an appropriate host cell to enable it to express the protein.

A host cell can be a prokaryotic cell, such as a bacterial cell; or a lower eukaryotic cell, such as a yeast cell; or a higher eukaryotic cell, such as a mammalian cell. Representative examples are: *Escherichia coli*, bacterial cells of *Streptomycess*; a fungal cell such as a yeast; a plant cell; an insect cell of *Drosophila* S2 or SD; an animal cell of CHO, NSO, COST, or 293 cell, and the like.

Transformation of host cells with recombinant DNA can be carried out using conventional techniques well known to the skilled in the art. When the host is a prokaryote such as *E. coli*, competent cells capable of absorbing DNA can be harvested after the exponential growth phase and treated with $CaCl_2$, the steps used are well known in the art. Another method is to use $MgCl_2$. If necessary, the transformation can also be carried out by means of electroporation. When the host is an eukaryote, the following DNA transfection methods are available: calcium phosphate coprecipitation, conventional mechanical methods such as microinjection, electroporation, liposome packaging, and the like.

The obtained transformants can be cultured by a conventional method to express a polypeptide encoded by the gene of the present invention. According to the host cell used, a medium used in the culture may be selected from a variety of conventional media. The host cell can be cultured under conditions suitable for the growth of the host cell. After the host cell grows to the appropriate cell density, the selected promoter is induced with a suitable method (such as temperature conversion or chemical induction), and the cells are incubated for a further period of time.

The protein in the method above may be included in the cells, or expressed on the cell membrane, or secreted out of the cell. If desired, the protein can be isolated and purified based on the physical, chemical and other properties by various isolation methods. These methods are well-known to those skilled in the art. The examples of these methods include, but are not limited to, conventional renaturation treatment, treatment with a protein precipitant (such as salt precipitation), centrifugation, cell lysis by osmosis, sonication, ultracentrifugation, molecular sieve chromatography (gel filtration), adsorption chromatography, ion exchange chromatography, high performance liquid chromatography (HPLC), and any other liquid chromatography, and the combination thereof.

In a preferred embodiment of the present invention, the amino acid sequence of Slit2D2 protein element is as follows:

```
                                        (SEQ ID NO.: 1)
LHCPAACTCSNNIVDCRGKGLTEIPTNLPETITEIRLEQNTIKVIPPGA

FSPYKKLRRIDLSNNQISELAPDAFQGLRSLNSLVLYGNKITELPKSLF

EGLFSLQLLLLNANKINCLRVDAFQDLHNLNLLSLYDNKLQTIAKGTFS

PLRAIQTMHLAQNPFICDCHLKWLADYLHTNPIETSGARCTSPRRLANK

RIGQIKSKKFRCS
```

In a preferred embodiment of the present invention, the amino acid sequence of HSA protein element is as follows:

```
                                        (SEQ ID NO.: 2)
DAHKSEVAHRFKDLGEENFKALVLIAFAQYLQQCPFEDHVKLVNEVTEF

AKTCVADESAENCDKSLHTLFGDKLCTVATLRETYGEMADCCAKQEPER

NECFLQHKDDNPNLPRLVRPEVDVMCTAFHDNEETFLKKYLYEIARRHP

YFYAPELLFFAKRYKAAFTECCQAADKAACLLPKLDELRDEGKASSAKQ

RLKCASLQKFGERAFKAWAVARLSQRFPKAEFAEVSKLVTDLTKVHTEC

CHGDLLECADDRADLAKYICENQDSISSKLKECCEKPLLEKSHCIAEVE

NDEMPADLPSLAADFVESKDVCKNYAEAKDVFLGMFLYEYARRHPDYSV

VLLLRLAKTYETTLEKCCAAADPHECYAKVFDEFKPLVEEPQNLIKQNC

ELFEQLGEYKFQNALLVRYTKKVPQVSTPTLVEVSRNLGKVGSKCCKHP

EAKRMPCAEDYLSVVLNQLCVLHEKTPVSDRVTKCCTESLVNRRPCFSA

LEVDETYVPKEFNAETFTFHADICTLSEKERQIKKQTALVELVKHKPKA

TKEQLKAVMDDFAAFVEKCCKADDKETCFAEEGKKLVAASQAALGL
```

Preferably, the amino acid sequence of the SlitD2-HSA fusion protein of the present invention is as follows:

```
                                        (SEQ ID NO.: 3)
LHCPAACTCSNNIVDCRGKGLTEIPTNLPETITEIRLEQNTIKVIPPGA

FSPYKKLRRIDLSNNQISELAPDAFQGLRSLNSLVLYGNKITELPKSLE

EGLFSLQLLLLNANKINCLRVDAFQDLHNLNLLSLYDNKLQTIAKGTFS

PLRAIQTMHLAQNPFICDCHLKWLADYLHTNPIETSGARCTSPRRLANK

RIGQIKSKKFRCSDAHKSEVAHRFKDLGEENFKALVLIAFAQYLQQCPF

EDHVKLVNEVTEFAKTCVADESAENCDKSLHTLFGDKLCTVATLRETYG

EMADCCAKQEPERNECELQHKDDNPNLPRLVRPEVDVMCTAFHDNEETE

LKKYLYEIARRHPYFYAPELLFFAKRYKAAFTECCQAADKAACLLPKLD

ELRDEGKASSAKQRLKCASLQKFGERAFKAWAVARLSQREPKAEFAEVS

KLVTDLTKVHTECCHGDLLECADDRADLAKYICENQDSISSKLKECCEK

PLLEKSHCIAEVENDEMPADLPSLAADFVESKDVCKNYAEAKDVFLGMF

LYEYARRHPDYSVVLLLRLAKTYETTLEKCCAAADPHECYAKVFDEFKP

LVEEPQNLIKQNCELFEQLGEYKEQNALLVRYTKKVPQVSTPTLVEVSR

NLGKVGSKCCKHPEAKRMPCAEDYLSVVLNQLCVLHEKTPVSDRVTKCC

TESLVNRRPCFSALEVDETYVPKEENAETETEHADICTLSEKERQIKKQ

TALVELVKHKPKATKEQLKAVMDDFAAFVEKCCKADDKETCFAEEGKKL

VAASQAALGL
```

The encoding DNA sequence thereof includes:

```
                                        (SEQ ID NO.: 4)
CTCTGGCTCCCCGGGGCgcgcTGTTTGCACTGCCCTGCCGCCTGTACCT

GTAGCAACAATATCGTAGACTGTCGTGGGAAAGGTCTCACTGAGATCCC

CACAAATCTTCCAGAGACCATCACAGAAATACGTTTGGAACAGAACACA

ATCAAAGTCATCCCTCCTGGAGCTTTCTCACCATATAAAAAGCTTAGAC

GAATTGACCTGAGCAATAAAGATCTCTGAACTTGCACCAGATGCTTTCC

AAGGACTACGCTCTCTGAATTCACTTGTCCTCTATGGAAATAAAATCAC

AGAACTCCCCAAAAGTTTATTTGAAGGACTGTTTTCCTTACAGCTCCAT

ATTGAATGCCAACAAGATAAACTGCCTTCGGGTAGATGCTTTTCAGGAT

CTCCACAACTTGAACCTTCTCTCCCTATATGACAACAAGCTTCAGACCA

TCGCCAAGGGGACCTTTTCACCTCTTGGCCATTCAAACTATGCATTTGG

CCCAGAACCCCTTTATTTGTGACTGCCATCTCAAGTGGCTAGCGGATTA

TCTCCATACCAACCCGATTGAGACCAGTGGTGCCCGTTGCACCAGCCCC

CGCCGCTGCAAACAAAAGAATTGGACAGATCAAAAGCAAGAAATTCCGT

TGTTCAGATGCACACAAGAGTGAGGTTGCTCATCGGTTTAAAGATTTGG

GAGAAGAAATTTCAAAGCCTTGGTGTTGATTGCTTTGCTCAGTATCTT

AGCAGTGTCCATTTGAAGATCATGTAAAATTAGTGAATGAAGTAACTGA

ATTTGCAAAAACATGTGTTGCTGATGAGTCAGCTGAAAATTGTGACAAA

TCACTTCATACCTTTTGGAGACAAATTAGCACAGTTGCAACTCTTCGT

GAAACCTATGGTGAAATGGCTGACTGCTGTGCAAAACAAGAACCTGAGA

GAAATGAATGCTTCTTGCAACACAAAGATGACAACCCAAACTCCCCCGA

TTGGTGAGACAGAGGTTGATGTGATGTGCACTGCTTTTCATGACAATGA
```

```
AGAGACATTTTTGAAAAAATACTTATATGAAATTGCCAGAAGACATCCT

TACTTTTATGCCCCGGAACCCTTTTCTTTGCTAAAAGGATAAAGCTGCT

TTTACAGAATGTTGCCAAGCTGCTGATAAAGCTGCCTGCCTGTTGCCAA

AGCTCGATGAACTTCGGGATGAAGGGAAGGCTTCGTCTGCCAAACAGGA

CTCAAGTGTGCCAGTCTCAAAAATTTGGAGAAAGAGCTTTCAAAGCATG

GGCAGTAGCTCGCCTGAGCCAGAGATTTCCCAAAGCTGAGTTTGCAGAA

GTTTCCAAGTTAGTGACAGATCTTACAAAGTCCACACGGAATGCTGCAT

GGAGATCTGCTTGAATGTGCTGATGACAGGGCGGACCTTGCCAAGTATA

TCTGTGAAAATCAAGATTCGATCTCCAGTAAACTGAAGGAATGCTGTGA

AAAACTCTGTTGGAAAAATCCCACTGCTTGCCGAAGTGGAAAATGATGA

GATGCCTGCTGACTTGCCTTCATTAGCTGCTGATTTTGTTGAAAGTAAG

GATGTTTGCAAAAACTATGCTGAGGCAAAGGATTCTTCCTGGGCATGTT

TTTGTATAATATGCAAGAAGGCATCCTGATTACTCTGTCGTGCTGCTGC

TGAGACTTGCCAAGACATATGAAACCACTCTAGAGAAGTGCTGTGCCGC

TGCAGATCCTCAGAATGCTATGCCAAAGTGTTCGATAATTTAAACCTCT

TGTGGAAGAGCCTCAGAATTTAATCAAACAAAATTGTGAGCTTTTTGAG

CAGCTTGGAGAGTACAAATTCCAGAATGCGCTATTAGTTCTTACACCAA

GAAAGTACCCCAAGTGCAACTCCAACTCTTGTAGAGGTCTCAAGAAACC

TAGGAAAAGTGGGCAGCAAATGTTGTAAACATCCTGAAGCAAAAAGAAT

GCCCTGTGCAGAAGACTATTATCCGTGGTCCTGAACCAGTTATGTTGTT

GCATGAGAAACGCCAGTAAGTGACAGAGTCACCAAATGCTGCACAGAA

TCCTTGGTGAACAGGCGACCATGCTTTTCAGCTCTGGAAGTCGATGAAC

ATACGTTCCCAAAGAGTTTAATGCTAAACATTCACCTTCCATGCAGATA

TATGCACACTTTCTGAGAAGGAGAGACAAATCAAGAAACAAACTGCACT

TGTTGAGCTCGTGAAACACAAGCCCAGGCAACAAAAGAGCAACTGAAAG

CTGTTTGGATGATTTCGCAGCTTTTGTAGAGAAGTGCTGCAAGGCTGAC

GATAAGGAGACCTGCTTTGCCGAGGAGGGTAAAAAACTTGTTGCTGCAA

GTCAACTGCCTTAGGCTTATAAGAATTCATTGATCATTAATCAGCCA
```

It should be understood that the term further comprises derivatives of the fusion protein of the present invention, which refer to polypeptides which are obtained by adding or replacing 1 to 3 amino acids, or deleting 1 to 2 amino acids from the fusion protein of the present invention, and still possess tumor inhibitory activity. These conservative variant polypeptides are preferably formed by carrying out the amino acid replacement according to Table 1.

TABLE 1

| Initial residue | Representative substitution | Preferred substitution |
| --- | --- | --- |
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |

TABLE 1-continued

| Initial residue | Representative substitution | Preferred substitution |
| --- | --- | --- |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

Once the relevant peptide sequences have been obtained and identified, the relevant peptide sequences in large quantities can be obtained by recombinant methods. This is usually done by cloning it into a vector, transferring it into a cell and then isolating the relevant peptide (fusion protein) from the proliferated host cell by conventional methods.

In addition, the relevant peptide sequences can be directly synthesized by chemical methods.

Peptide Linker

A fusion protein is provided by the present invention, which can optionally contain a peptide linker. Size and complexity of the peptide linker may affect protein activity. In general, the peptide linker should have sufficient length and flexibility to ensure that the two proteins attached have sufficient degrees of freedom in space to function and avoid the influence of the formation of α-helix or (3-sheet and the like in the peptide linker on the stability of the fusion protein.

The length of the linker peptide is generally 0 to 10 amino acids, preferably 1 to 5 amino acids.

Pharmaceutical Composition and Administration Method

A composition is further provided by the present invention, which comprises an effective amount of the fusion protein of the present invention, and a pharmaceutically acceptable carrier. In general, the fusion protein of the present invention may be formulated in a non-toxic, inert and pharmaceutically acceptable aqueous carrier medium, wherein the pH is typically about 5-8, and preferably, pH is about 6-8.

As used herein, the term "effective amount" or "effective dosage" refers to an amount which can achieve function or activity in human and/or animal and is acceptable by human and/or animal, such as, 0.001-99 wt %; preferably, 0.01-95 wt %, more preferably, 0.1-90 wt %.

As used herein, "pharmaceutically acceptable" component is a substance which is suitable for human and/or mammal without undue adverse side effects (such as toxicity, stimulation and allergic reaction) with a reasonable benefit/risk ratio. The term "pharmaceutically acceptable carrier" refers to a carrier for administration of a therapeutic agent including various excipients and diluents.

The pharmaceutical composition of the present invention comprises a safe and effective amount of the fusion protein of the present invention and a pharmaceutically acceptable carrier. Such carriers include (but are not limited to) saline, buffer solution, glucose, water, glycerol, ethanol, and combinations thereof. In general, the pharmaceutical preparation should match the mode of administration. The pharmaceutical composition of the present invention can be formulated into the form of injection, such as formulated with saline or an aqueous solution containing glucose and other adjuvants by using conventional methods. The pharmaceutical composition is preferably produced under sterile conditions. The dose of the active ingredient is a therapeutically effective amount. The pharmaceutical formulations of the present invention may also be formulated as a sustained release preparation.

The effective amount of the fusion protein of the present invention may be varied depending on the mode of administration and the severity of the disease to be treated. The selection of preferred effective amount can be determined depending on various factors by those skilled in the art (e.g., via clinical trials). The factors include, but are not limited to: the pharmacokinetic parameters of the fusion protein of the present invention, such as bioavailability, metabolism, half-life and the like; the severity of the patient's disease to be treated, the weight of the patient, the immune status of the patient, administration way and the like. Typically, when the fusion protein of the present invention is administered at a dose of about 0.5 mg-5 mg/kg animal body weight (preferably 2 mg-4 mg/kg animal body weight), the satisfactory results can be obtained for tumor patient. For example, according to the urgent requirements of the treatment status, several divided doses can be administered daily, or the dosage can be reduced proportionally.

The main advantages of the present invention are:

(1) The slit2D2-HSA fusion protein of the present invention has a broad spectrum of anti-tumor effects including tumor metastasis inhibitory effects on lung cancer (A549), breast cancer (MDA-MB-231), pancreatic cancer (ASPC-1), melanoma (A435, MB-435S) and liver cancer (HepG2), which reflects its broad-spectrum anti-tumor effects;

(2) Slit2 shows different effects (promotion or inhibition) in different tumor cells, but the fusion protein molecules developed by the present invention exhibits inhibitory effects on the targeted tumor cells.

(3) The slit2D2-HSA fusion protein of the present invention significantly inhibits the migration of vascular endothelial cells, thereby inhibiting the supply of tumor nutrition and exhibiting the effect of inhibiting tumor growth in animals;

(4) The slit2D2-HSA fusion protein of the present invention is safe, with no obvious toxic and side effects on animals and with a long half-life.

The invention will be further illustrated with reference to the following specific examples. It is to be understood that these examples are only intended to illustrate the invention, but not to limit the scope of the invention. For the experimental methods in the following examples without particular conditions, they are performed under routine conditions (eg. Sambrook et al., Molecular Cloning: A Laboratory Manual (New York: Cold Spring Harbor Laboratory Press, 1989) or as instructed by the manufacturer. Unless otherwise specified, all percentages, and parts are calculated by weight. Unless otherwise specified, experimental materials and reagents used in the following examples are commercially available.

Example 1: The Preparation for SlitD2-HSA Fusion Protein 1.1 Preparation for SlitD2-HSA Fusion Protein According to the slit2 sequence [GenBank: EAW92793.1], a fusion expression vector for constructing the second domain of Slit2D2 (Hohenester 2008) and human serum albumin HSA was designed and constructed. Slit2D2 and HSA gene fragments were obtained by whole genome synthesis and used as a template to amplify the sequence of Slit2D2 gene by PCR using primers of T62F and T62R and to amplify the sequence of HSA gene using primers of T60F3 and T59R, respectively. The 674 bp and 1783 bp of PCR products as described above were purified with gel extraction kit. The pCDNA3.1 vector (Invitrogen) containing a CMV promoter was digested with BssH II and EcoR I, and the two PCR products and the enzyme digestion vector were subjected to a seamless connection reaction, followed by transforming TOP10 strain (purchased from Shanghai Solarbio Biotech Co., Ltd.), being screened by ampicillin and selecting positive clones to obtain the vector which was confirmed to be successfully constructed by sequencing. Plasmid DNA was extracted with endotoxin-free DNA extraction kit and used to transfect EXPI293 cells. EXPI293 cells (purchased from Life Technologies) were cultured, transfected at a density of $2.5 \times 10^6$ cells/ml, and the supernatants were collected after 5 days of transfection. The supernatant was extracted from the culture of EXPI293 after high-speed centrifugation and the SlitD2-HSA fusion protein was purified by ion exchange chromatography. The molecular weight of the target protein was detected by SDS-PAGE and the protein purity was measured by HPLC.

The primer sequences in this example are as follows:

```
>T62F
                                        (SEQ ID NO.: 5)
CTCTGGCTCCCCGGGGCgcgcTGTTTGCACTGCCCTGCCGCCTGTACC >T62R
                                        (SEQ ID NO.: 6)
GCAACCTCACTCTTGTGTGCATCTGAACAACGGAATTTCTTGCTT >T60F3
                                        (SEQ ID NO.: 7)
GATGCACACAAGAGTGAGGTTGC >T59R
                                        (SEQ ID NO.: 8)
TGGCTGATTAATGATCAATGAATTCTTATAAGCCTAAGGCAGCTTG
```

Figure 1:
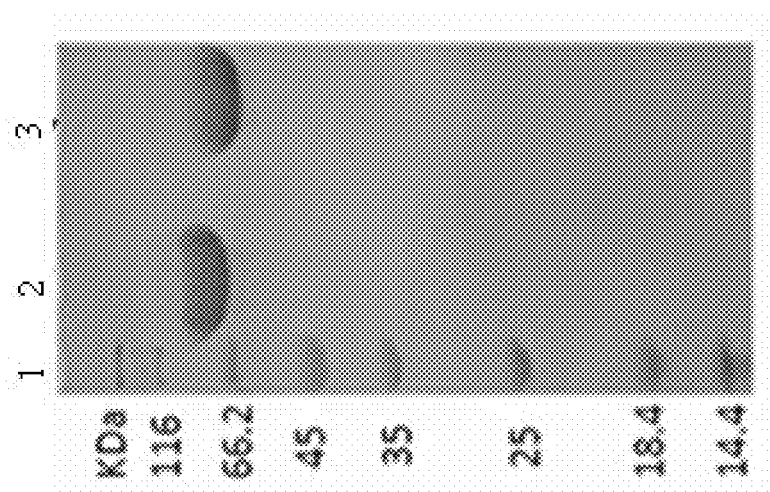
FIG. 1 shows an electrophoresis identification result for the SlitD2-HSA fusion protein.

FIG. 1 shows the identification results of SlitD2-HSA recombinant protein expression, with an electrophoresis pattern of 12% SDS-PAGE electrophoresis, lanes 1-3 were molecular weight markers, electrophoresis results under the reduction conditions and non-reduction conditions, respectively. FIG. 2 shows the results of HPLC detection (SEC-HPLC; G3000swxl; 0.5 ml/min; 40 min; UV280), indicating that a fusion protein with a very high purity was prepared in this Example. The above results show that the molecular weight of the constructed fusion protein is in line with the expectation. In this example, the SlitD2-HSA fusion protein was successfully constructed and prepared.

Example 2 the Detection of In Vitro Broad Spectrum Anti-Tumor Metastatic Activity of SlitD2-HSA Protein 2.1 In Vitro Activity Test A. The Establishment of Transwell Tumor Metastasis Model In Vitro The tumor cells were digested and dispersed, and 15,000 cells were added to the upper layer of the transwell chamber, with a total volume of 100 μl, without serum. Each group contained different concentrations of drugs in triplicate for each group. 600 μl of medium containing 10% serum was added into the lower chamber, and SDF1 at a final concentration of 10 Nm was added. Except the NC group, SDF1 was added into the lower layer of the rest of the groups. After 24 hours the chambers were fixed with 4% paraformaldehyde, the upper membrane cells were gently wiped off and the lower membrane cells were stained with DAPI. The stained cells of the lower membrane were photographed under a fluorescence microscope, and 5 fields of views under 20× objective were randomly selected for each chamber. The number of cells in each photograph were counted. The slit2N protein used in the experiment was the N-fragment of slit2 full-length protein, which was served as a control protein (purchased from sigma company, item No. of SRP3155).

The following cell lines were tested in vitro to determine the anti-tumor spectrum of drugs.

Lung cancer: A549; breast cancer: MCF-7/ADR, MDA-MB-231; melanoma: MDA-MB-435S, A431; liver cancer: HepG2, SMMC7721; pancreatic cancer: ASPC-1. The above cell lines are available through commercial channels.

B. Human Umbilical Vein Endothelial Cell (HUVEC) Migration Sssay:

1. Starvation was conducted for HUVEC for 12 hours.
2. Below the transwell chamber, 600 μL of basic medium (without serum and other growth factors) containing VEGF (50 ng/mL) and different proteins was added and above the chamber, the starved cells resuspended in 100 μL basic medium (4×10$^4$) and different proteins were added. Each group was made in triplicate.
3. The cells were incubated in 5% $CO_2$ incubator at 37° C., fixed and stained with crystal violet after 6 hours of incubation. The cells above the chamber were gently wiped off with a cotton swab and a photo (with a magnification of 10×1.6 times) was taken for statistical analysis.

Calculation Formula for Inhibition Rate

Inhibition rate=(number of cell migrated in HSA group−number of cell migrated in administration group)/(number of cell migrated in HSA group−number of cell migrated in PBS group)*100%

Figure 3:
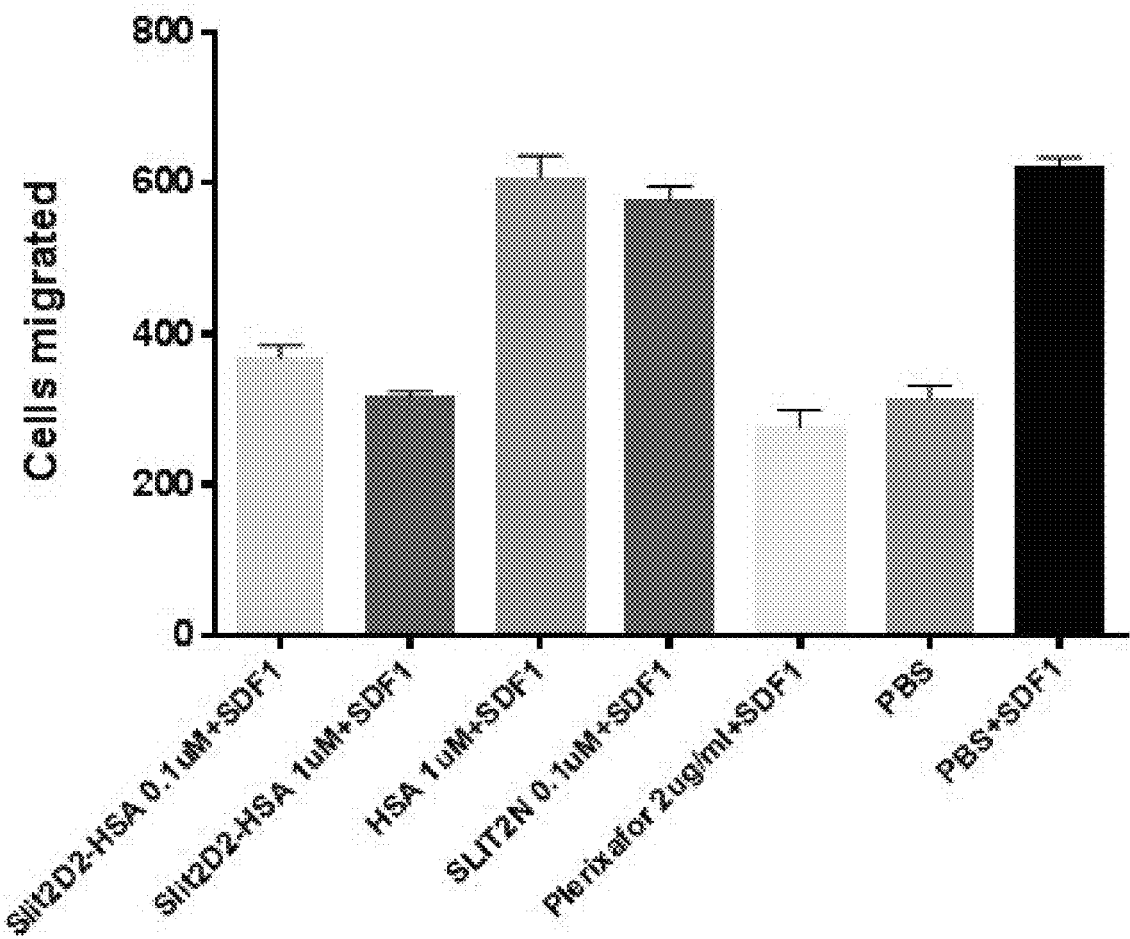
FIG. 3 shows the inhibitory activity for lung cancer A549, Slit2D2-HSA can inhibit the migration of lung cancer A549 cells induced by SDF-1. The inhibitory rate of Slit2D2-HSA is 82% (P<0.001) at the concentration of 0.1 µM; the inhibition rate is 98% (P<0.001) at the concentration of 1 µM; and Slit2N has no significant inhibitory effect on A549 at the concentration of 0.1 µM.

FIG. 3 shows an inhibitory activity for lung cancer A549. Slit2D2-HSA can inhibit the migration of lung cancer A549 cells induced by SDF-1. The inhibitory rate of Slit2D2-HSA is 82% (P<0.001) at the concentration of 0.1 Um; The inhibition rate is 98% P<0.001 at the concentration of 1 Um; Slit2N (Slit2N is the N-terminus of the slit2 protein, which is about 140 kd and contains the D1-D4 domain of slit2 and multiple EGF repeats, purchased from Sigma) has no significant inhibitory effect on A549 at the concentration of 0.1 Um.

Figure 4:
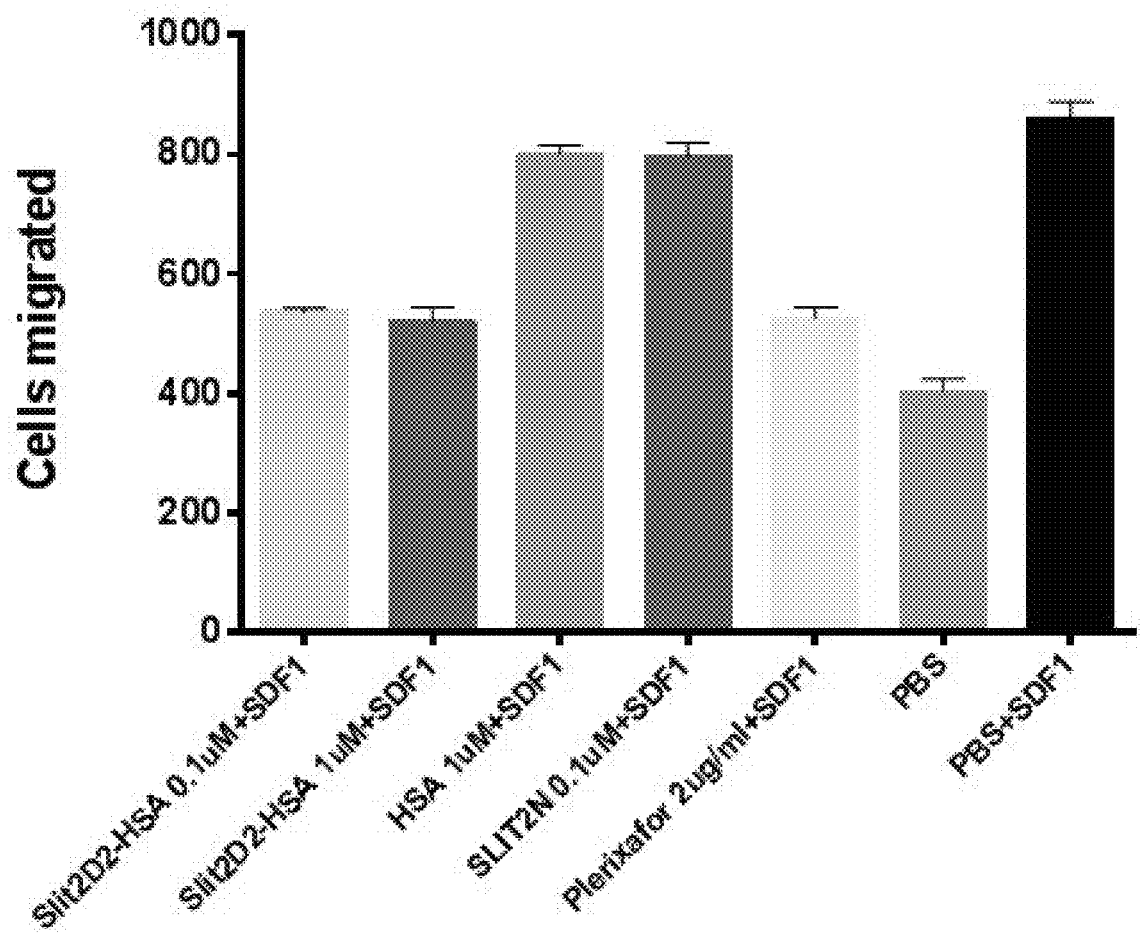
FIG. 4 shows the inhibitory activity for hepatoma HepG2. Slit2D2-HSA can inhibit the migration of hepatoma cell HepG2 induced by SDF-1. The inhibitory rate is 67% at the concentration of 0.1 µM, P<0.001; the inhibition rate is 71% at the concentration of 1 µM, P<0.001. Slit2N has no significant inhibitory effect on HepG2 at the concentration of 0.1 µM.

FIG. 4 shows the inhibitory activity for hepatoma HepG2. Slit2D2-HSA can inhibit the migration of hepatoma cell HepG2 induced by SDF-1. The inhibitory rate is 67% at the concentration of 0.1 Um, P<0.001; the inhibition rate at the concentration of 1 Um is 71%, P<0.001. Slit2N has no significant inhibitory effect on HepG2 at the concentration of 0.1 Um.

Figure 5:
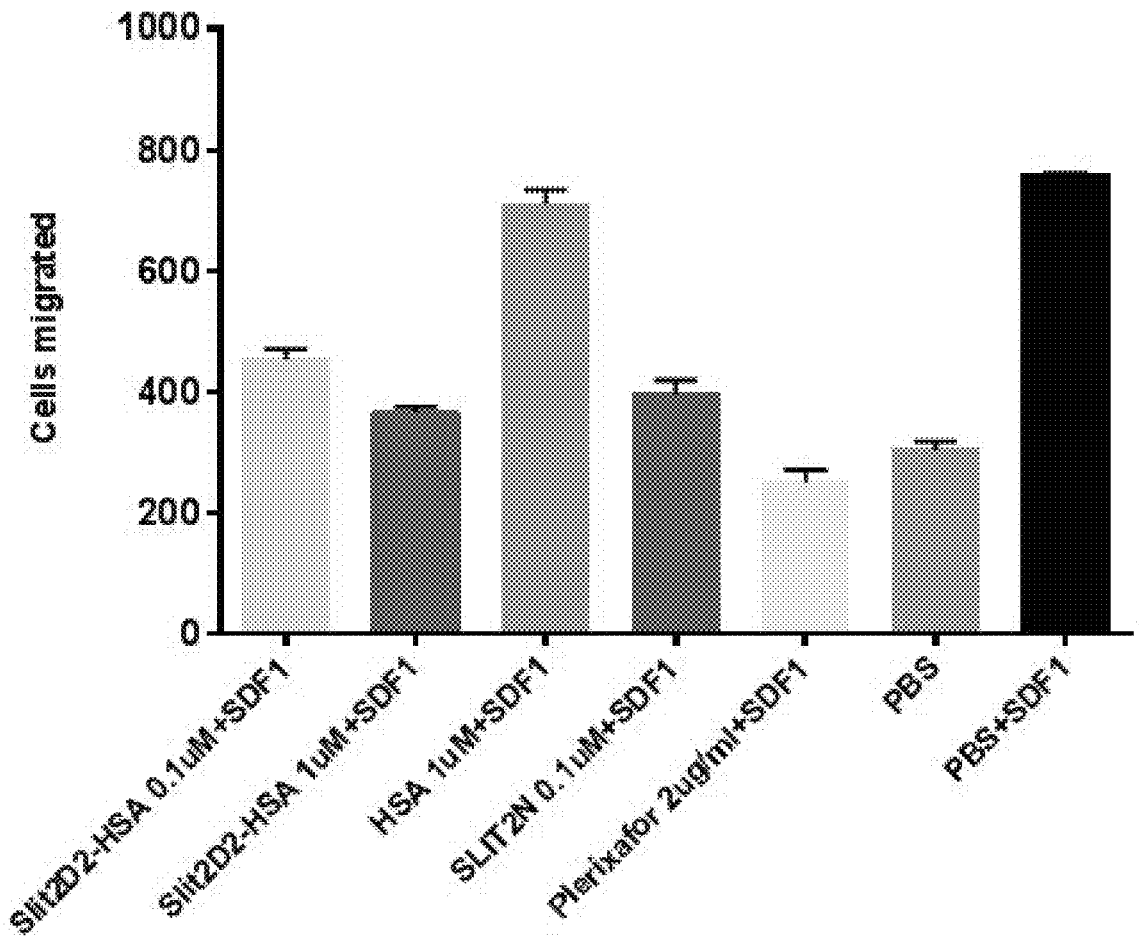
FIG. 5 shows the inhibitory activity for melanoma. Slit2D2-HSA can inhibit the migration of melanoma MDA-MB-435S cells induced by SDF-1. The inhibitory rate is 63% (P<0.001) at the concentration of 0.1 µM; the inhibitory rate is 84% (P<0.001) at the concentration of 1 µM; and the inhibitory rate of Slit2N on the migration of MDA-MB-435S cells is 77% (P<0.001) at a concentration of 0.1 µM.

FIG. 5 shows the inhibitory activity for melanoma. Slit2D2-HSA can inhibit the migration of melanoma MDA-MB-4355 cells induced by SDF-1. The inhibitory rate is 63% (P<0.001) at the concentration of 0.1 Um; and the inhibitory rate is 84% (P<0.001) at the concentration of 1 Um. The inhibitory rate of Slit2N on the migration of MDA-MB-4355 cells is 77% (P<0.001) at a concentration of 0.1 Um.

Figure 6:
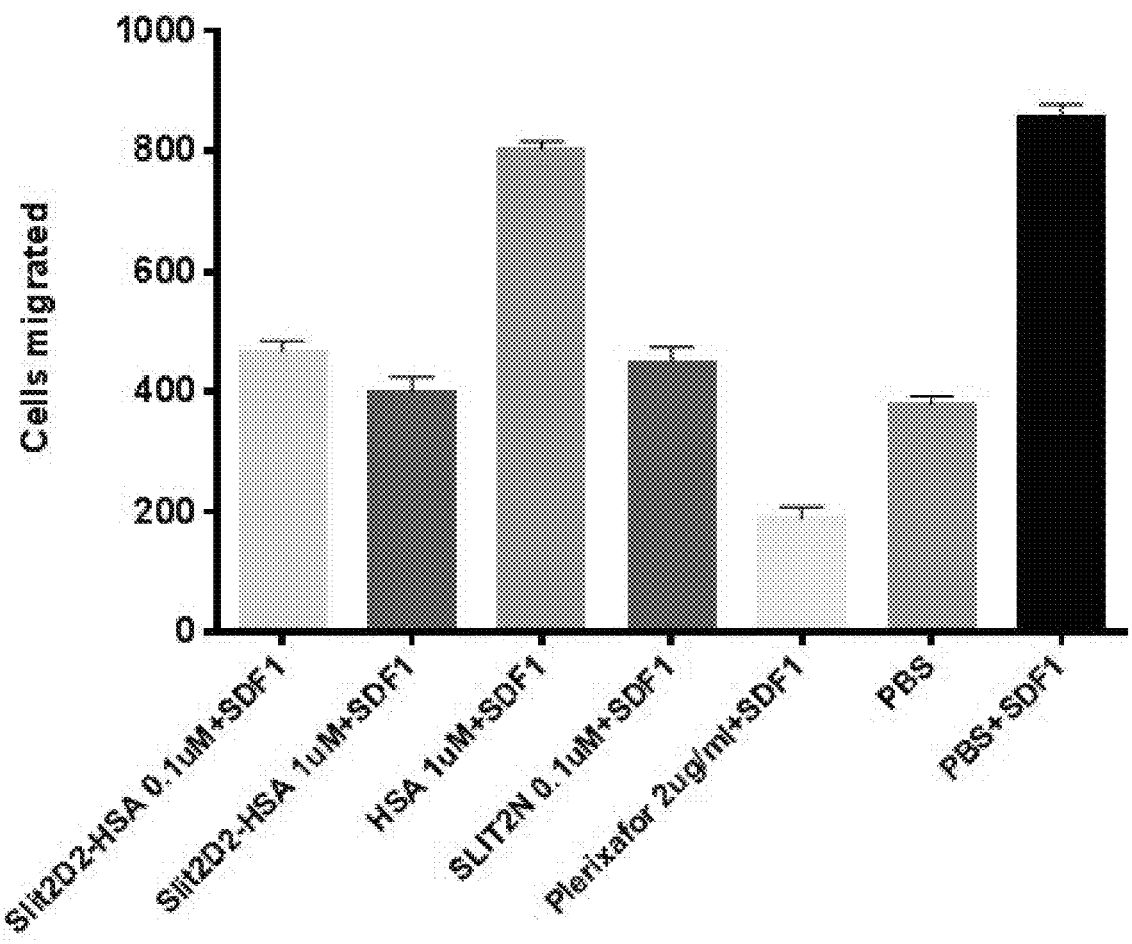
FIG. 6 shows the inhibitory activity for pancreatic cancer ASPC-1. Slit2D2-HSA can inhibit the migration of pancreatic cancer ASPC-1 cells induced by SDF-1. The inhibition rate is 79% (P<0.001) at the concentration of 0.1 µM; the inhibitory rate is 95% (P<0.001) at a concentration of 1 µM. The inhibitory rate of Slit2N on the migration of pancreatic cancer ASPC-1 cells is 83% at the concentration of 0.1 µM (P<0.001).

FIG. 6 shows pancreatic cancer ASPC-1. Slit2D2-HSA can inhibit the migration of pancreatic cancer ASPC-1 cells induced by SDF-1. The inhibition rate is 79% (P<0.001) at the concentration of 0.1 Um. The inhibitory rate is 95% (P<0.001) at the concentration of 1 Um. The inhibitory rate of Slit2N on the migration of pancreatic cancer ASPC-1 cells is 83% at the concentration of 0.1 Um (P<0.001).

Figure 7:
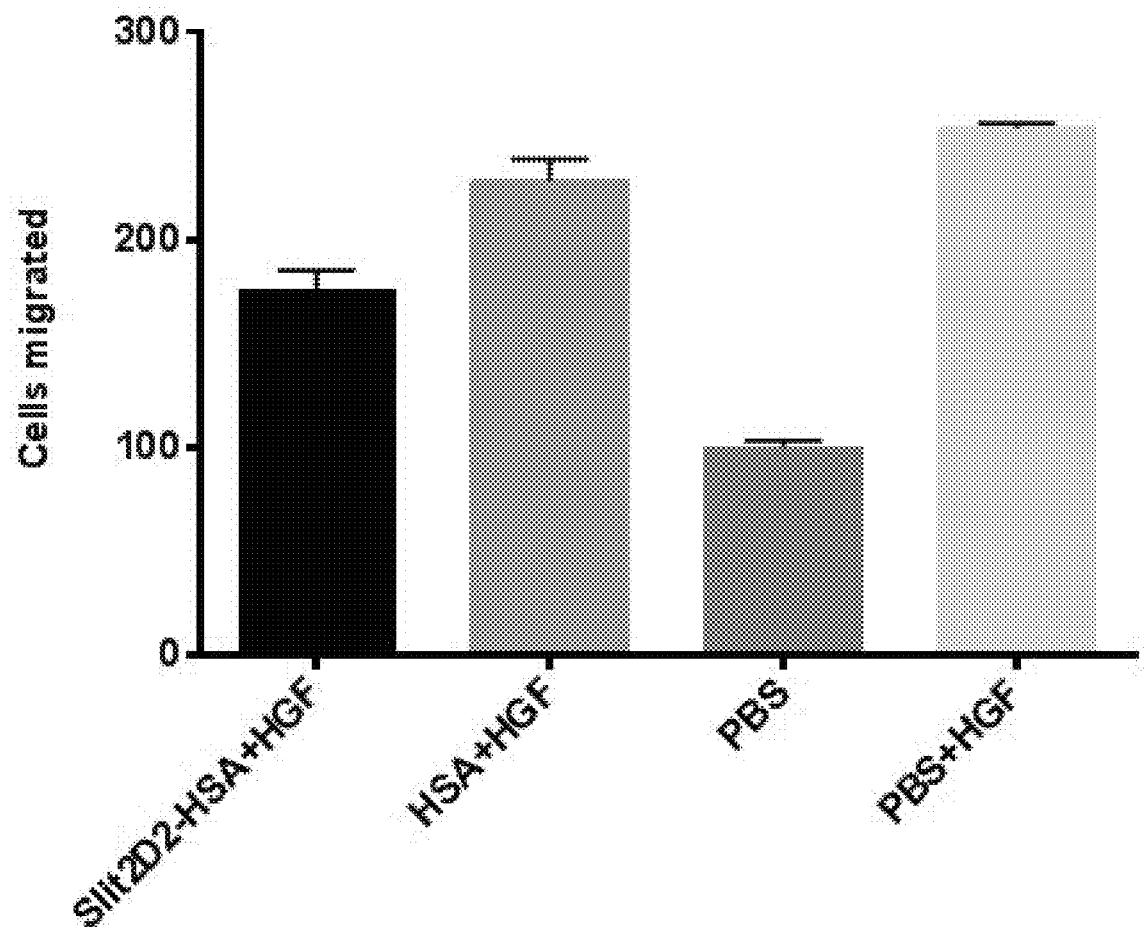
FIG. 7 shows the inhibitory activity for breast cancer MDA-MB-231 (HGF-induced metastasis). Slit2D2-HSA can inhibit HGF-induced migration of breast cancer MDA-MB-231 cells, and the inhibitory rate is 41% (P<0.01) at the concentration of 1 µM.

FIG. 7 shows the inhibitory activity for breast cancer MDA-MB-231 (HGF-induced metastasis). Slit2D2-HSA can inhibit HGF-induced migration of breast cancer MDA-MB-231 cells, and the inhibitory rate is 41% (P<0.01) at the concentration of 1 Um.

Figure 8:
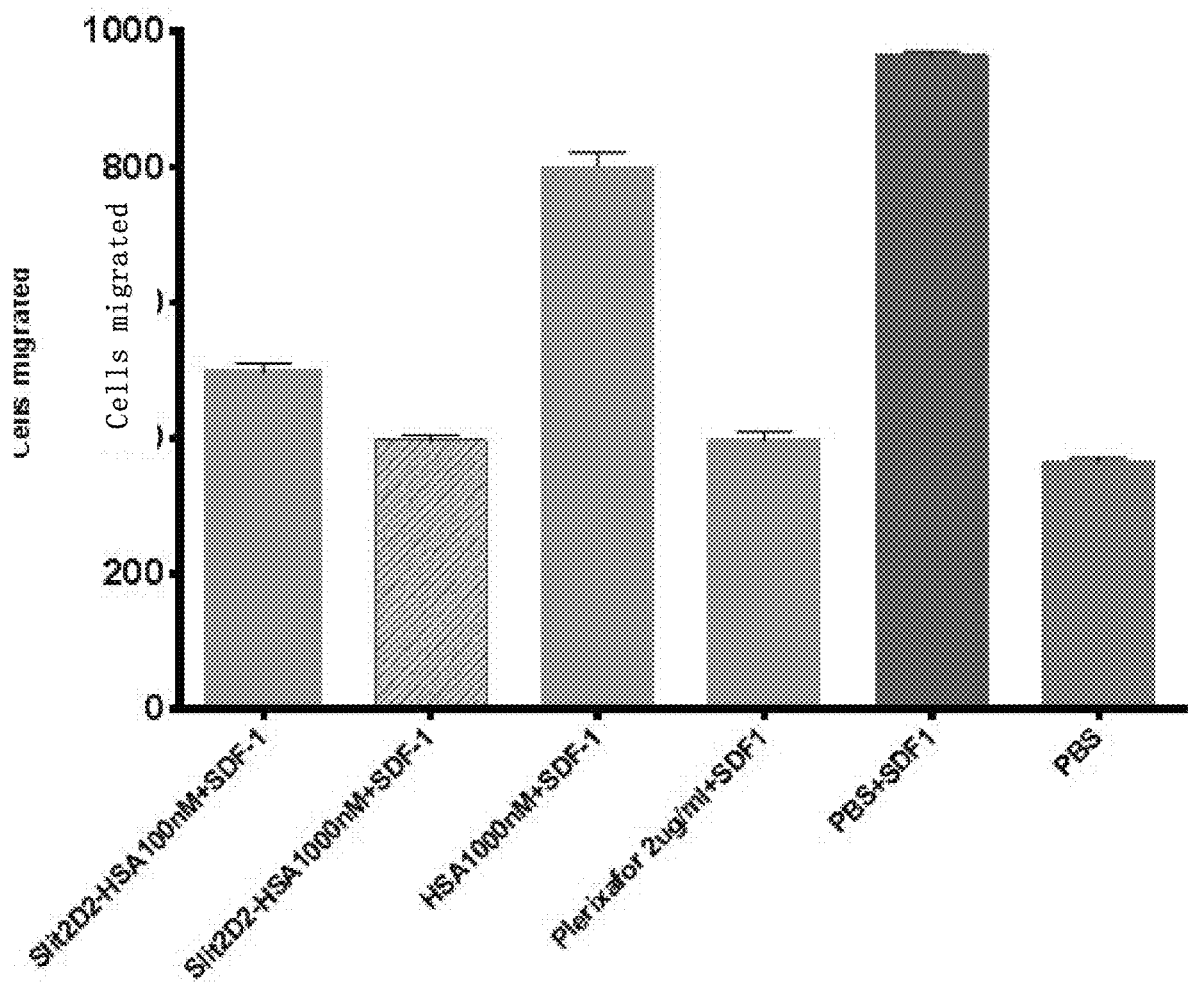
FIG. 8 shows the inhibitory activity for breast cancer MDA-MB-231 (SDF-1 induced metastasis). Slit2D2-HSA can inhibit the migration of breast cancer MDA-MB-231 cells induced by SDF-1, the inhibition rate is 69% (P<0.001) at the concentration of 0.1 µM; and the inhibition rate is 92% (P<0.001) at the concentration of 1 µM.

FIG. 8 shows the inhibitory activity for breast cancer MDA-MB-231 (SDF-1 induced metastasis). Slit2D2-HSA can inhibit the migration of breast cancer MDA-MB-231 cells induced by SDF-1, the inhibition rate is 69% (P<0.001) at the concentration of 0.1 Um; and the inhibition rate is 92% (P<0.001) at the concentration of 1 Um.

Figure 9:
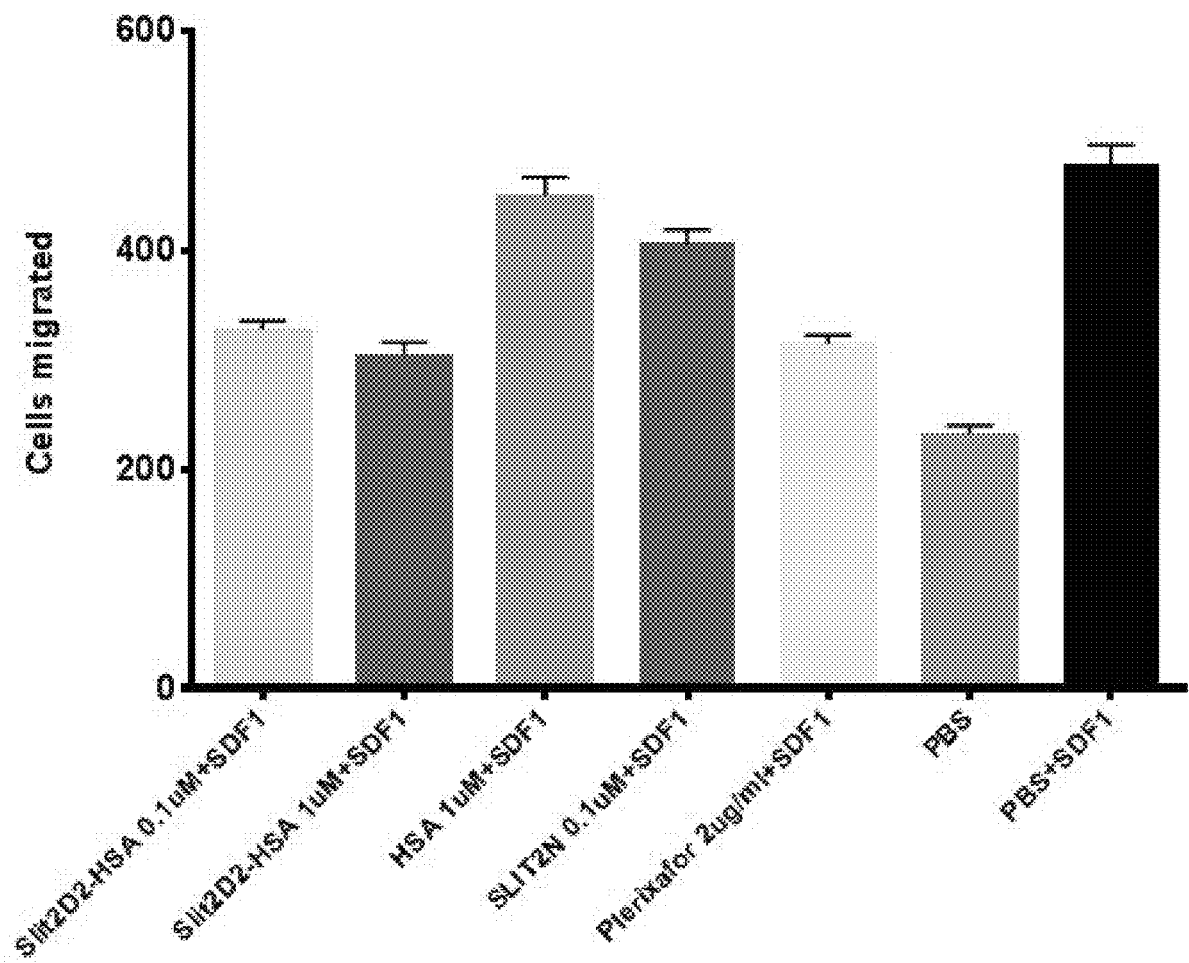
FIG. 9 shows the inhibitory activity for melanoma A375. Slit2D2-HSA can inhibit the SDF-1-induced migration of melanoma A375 cells with a 54% inhibition rate at the concentration of 0.1 µM (P<0.001) and a 66% (P<0.001) at the concentration of 1 µM. There is no significant inhibitory effect for SlitN on the migration of melanoma A375 cells at the concentration of 0.1 µM (P<0.001).

FIG. 9 shows the inhibitory activity for melanoma A375. Slit2D2-HSA can inhibit the SDF-1-induced migration of melanoma A375 cells with a 54% inhibition rate at the concentration of 0.1 Um (P<0.001); and the inhibition rate is 66% (P<0.001) at the concentration of 1 Um. There is no significant inhibitory effect for SlitN on the migration of melanoma A375 at the concentration of 0.1 Um.

Figure 10:
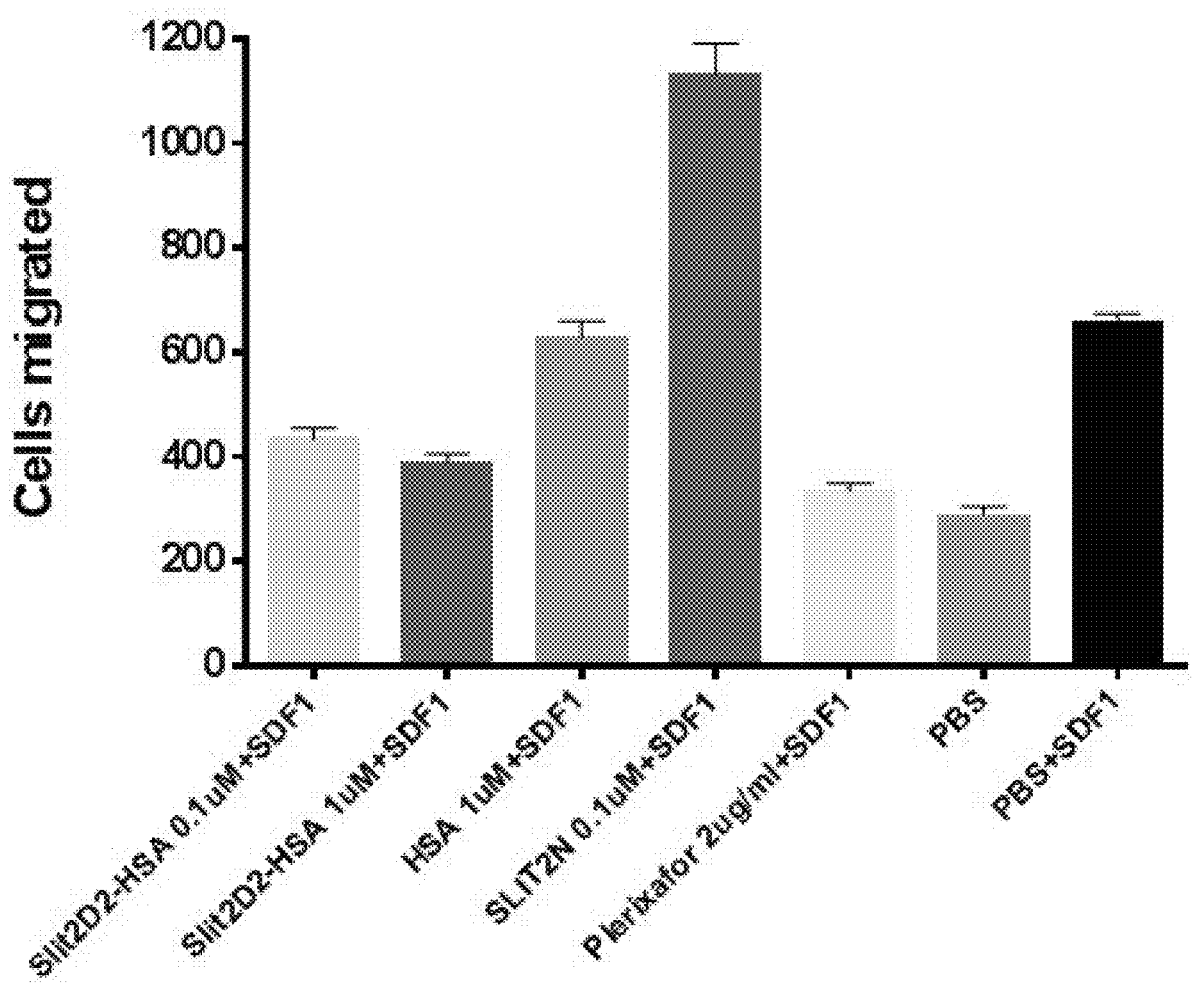
FIG. 10 shows the inhibitory activity for breast cancer MCF-7/ADR. Slit2D2-HSA can inhibit the migration of breast cancer MCF-7/ADR cells induced by SDF-1. The inhibitory rate is 58% at the concentration of 0.1 µM (P<0.001). The inhibitory rate is 71% (P<0.001) at the concentration of 1 µM. There is a significant promoting effect for SlitN on the migration of MCF-7/ADR cells at the concentration of 0.1 µM, contrary to the effect of Slit2D2-HSA.

FIG. 10 shows the inhibitory activity for breast cancer MCF-7/ADR. Slit2D2-HSA can inhibit the migration of breast cancer MCF-7/ADR cells induced by SDF-1. The inhibitory rate is 58% at the concentration of 0.1 Um (P<0.001). The inhibitory rate is 71% (P<0.001) at the concentration of 1 Um. There is a significant promoting effect for SlitN on the migration of MCF-7/ADR cells at the concentration of 0.1 Um, contrary to the effect of Slit2D2-HSA.

Figure 11:
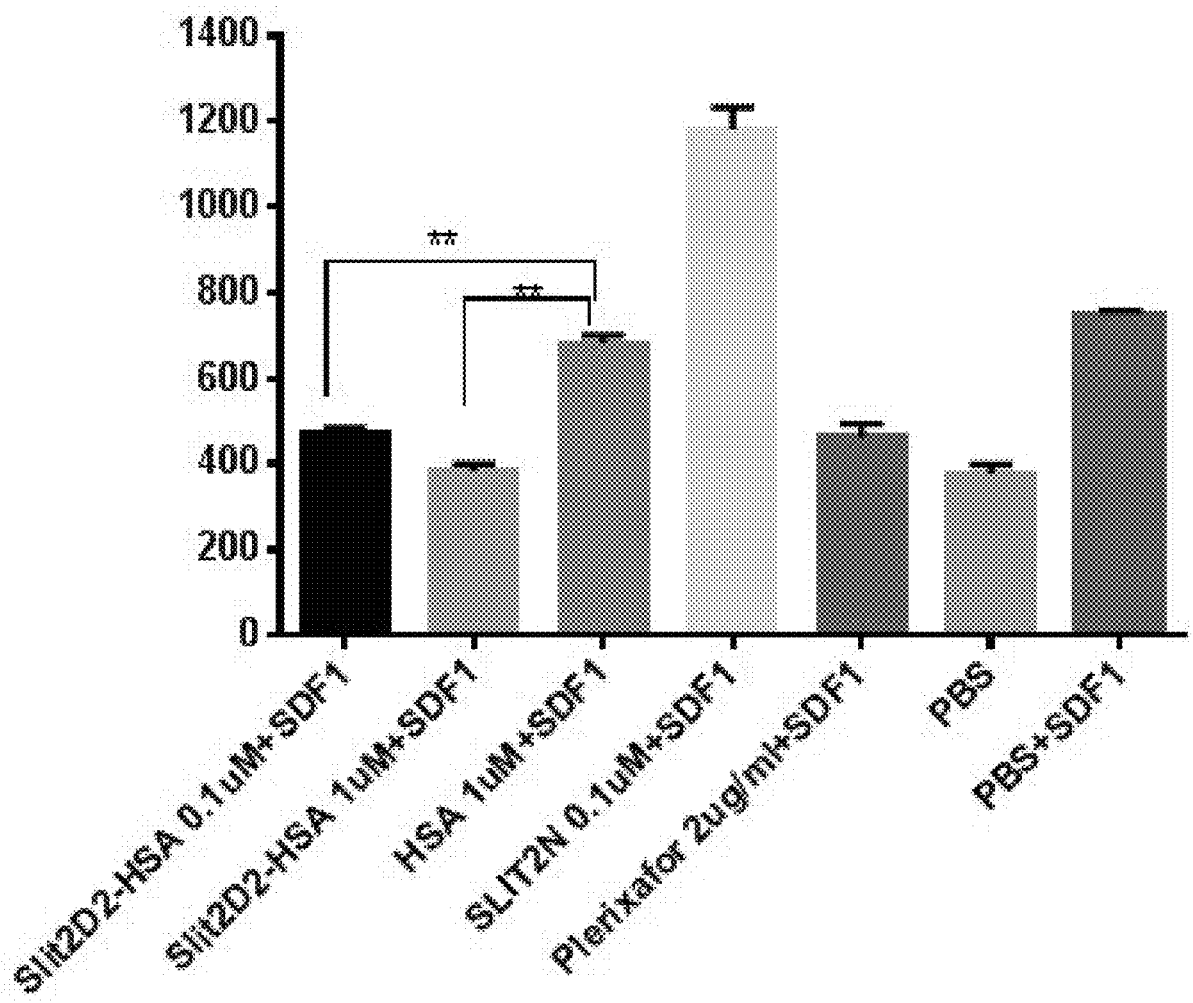
FIG. 11 shows the inhibitory activity for hepatoma SMMC7721. Slit2D2-HSA can inhibit the migration of hepatoma SMMC7721 cells induced by SDF-1. The inhibitory rate is 68% (P<0.001) at the concentration of 0.1 µM. The inhibitory rate is 99% (P<0.001) at the concentration of 1 µM. There is a significant promoting effect for SlitN on the migration of SMMC7721 cells at the concentration of 0.1 µM, contrary to the effect of Slit2D2-HSA.

FIG. 11 shows the inhibitory activity for hepatoma SMMC7721. Slit2D2-HSA can inhibit the migration of hepatoma SMMC7721 cells induced by SDF-1. The inhibitory rate is 68% (P<0.001) at the concentration of 0.1 Um. The inhibitory rate is 99% (P<0.001) at the concentration of 1 Um. There is a significant promoting effect for SlitN on the migration of SMMC7721 cells at the concentration of 0.1 Um, contrary to the effect of Slit2D2-HSA.

Figure 12:
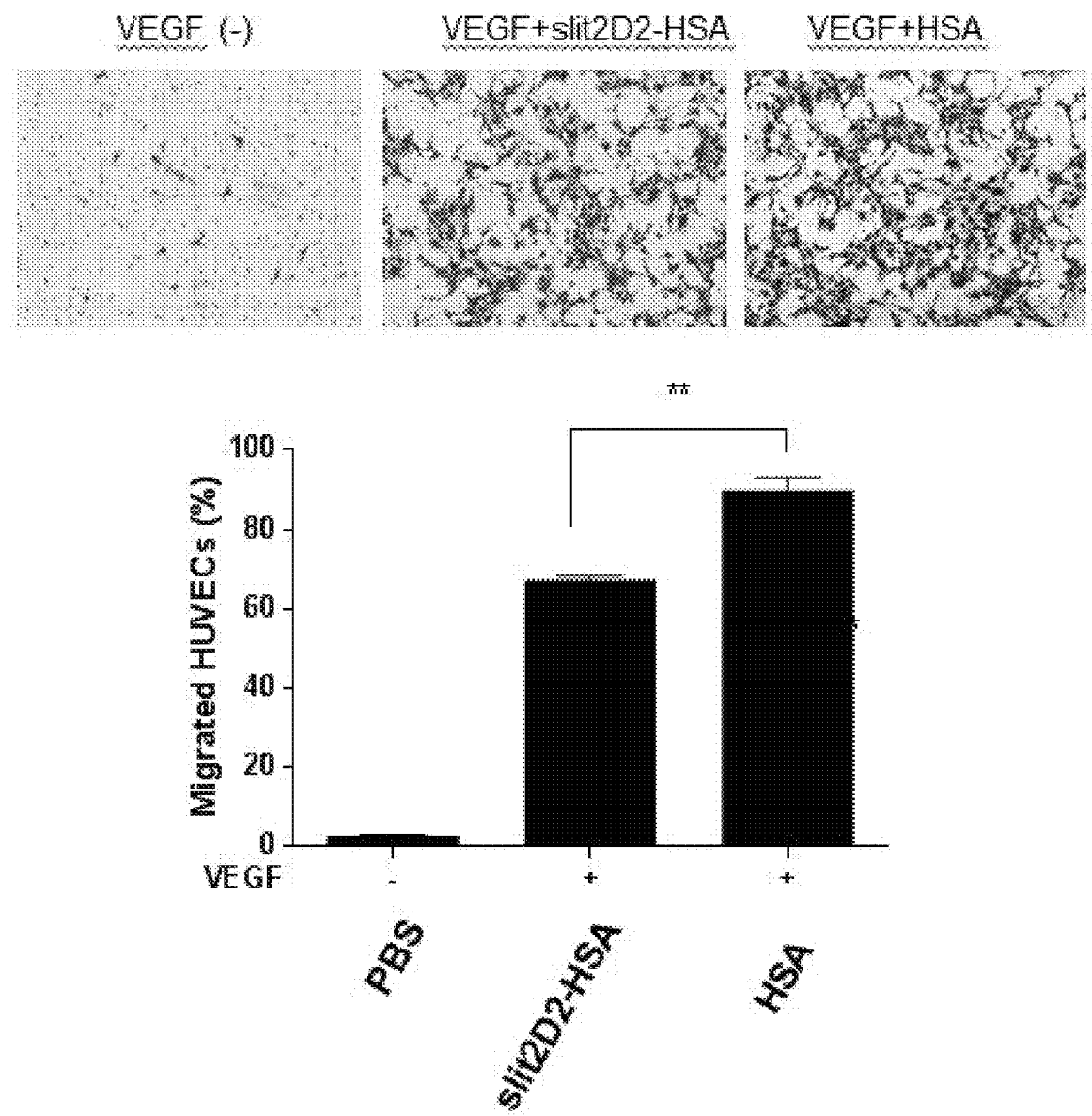
FIG. 12 shows the results of vascular endothelial cell migration assay. Slit2D2-HSA can inhibit VEGF-induced migration of vascular endothelial cells.

FIG. 12 shows the results of vascular endothelial cell migration assay. Slit2D2-HSA can inhibit VEGF-induced migration of vascular endothelial cells.

Example 3 Pharmacodynamics Study on the Metastatic Model Obtained from the Injection of Human Breast Cancer MDA-MB-231-Luc Through Tail Vein 3.1 Cell Lines and Cell Preparation MDA-MB-231-Luc cell line: purchased from Nanjing Genscript Biotechnology Co., Ltd.

The cell line was inoculated in RPMI1640 containing 10% of fetal bovine serum and 1% of penicillin/streptomycin and cultured at 37° C. in a 5% of $CO_2$ constant temperature incubator.

3.2 Experimental Animals

Germline and number: 32 SCID-Beige mice.

Age and sex: 6-8 weeks old, ♀, 18-22 g

Supplier: Shanghai Lingchang biotechnology Co., Ltd.

Rearing environment: SPF animal room 3.3 Reagents

RPMI1640 medium: Hyclone, Cat. No.: SH30809.01B; fetal bovine serum: Biological Industries, Cat. No.: 04-001-1a; penicillin/streptomycin: Gibco, Cat. No.: 15070-063; 0.25% of trypsin-EDTA: Invitrogen, Cat. No.: 25200-072; HBSS −/−: Invitrogen, Cat. No.: 14175; tested drug: Slit2D2-HSA, concentration: 1 mg/ml, specifications: 500 ul/stick*20, traits: liquid, storage conditions: −80° C.; Plerixafor, specifications: 5 mg, traits: white powder, storage conditions: −20° C., drug preparation: the tested drug in each group was diluted with PBS to an appropriate concentration for administration and the diluted solution was stored at 4° C. until use. The positive control drug, Plerixafor, was dissolved in PBS to an appropriate concentration for administration and the solution was stored at 4° C. until use.

3.4 Experimental Procedure

Animal Inoculation

MDA-MB-231-Luc cells were amplified and 32 SCID mice were subjected to the tail vein injection at a dose of $1.5×10^6$ cells/mouse, respectively, and followed by the subsequent pharmacodynamics studies.

Grouping and Administration

On the day of modeling, mice were randomly divided into 4 groups, 8 mice in each group, and treated with the drugs. Specific grouping and administration are shown in Table 1:

TABLE 1 animal grouping and administration

| Group | n | drug therapy | dose (mg/kg) | volume of administration | route of administration | frequency and period of administration |
|---|---|---|---|---|---|---|
| 1 | 8 | solvent control (PBS) | — | 10 ml/kg | intraperitoneal injection (i.p.) | once every two days (qd) × 21 days |
| 2 | 8 | positive control Plerixafor | 5 | 10 ml/kg | (i.p.) | once a day (qd) × 21 days |
| 3 | 8 | the tested drug (high concentration group) | 4.5 | 10 ml/kg | (i.p.) | once every two days (qd) × 21 days |
| 4 | 8 | the tested drug (low concentration group) | 0.45 | 10 ml/kg | (i.p.) | once every two days (qd) × 21 days |

Observation and Detection

Animal status was observed every day after inoculation to the end of the experiment, and the animal would be treated or dissected by veterinary if it was found to be sick or abnormally dead.

During drug administration, the drug administration needs to be stopped if the weight of animal has decreased by more than 20%.

In the experimental process, if the tumor-bearing mouse is dead, estimate timely and record the time of death, dissect for autopsy. If the dissection can not be done in time, it was placed in the refrigerator at −20° C. to reduce tissue autolysis; if the status of tumor-bearing mice is very poor or dying, they should be euthanized according to animal welfare; and they should also be euthanized when the weight loss has exceeded 30% of basal body weight.

Animal weight: body weight was weighed twice a week and recorded.

Measurement of tumor growth: it was taken as day 0 on the day of cell inoculation, animal bioluminescence imaging in vivo was detected at Day 0, Day 3, Day 8, Day 13, Day 17, and Day 21, respectively, 6 timings in total.

Tumor metastasis rate=(fluorescence value on Day 21−fluorescence value on Day 8)/fluorescence value on Day 8

The smaller the tumor metastasis rate was, the stronger the ability of the drug to inhibit tumor metastasis had.

(The tumor was in a stable phase in the body in the first seven days and showed the growth and metastasis trends from day 8)

Figure 13:
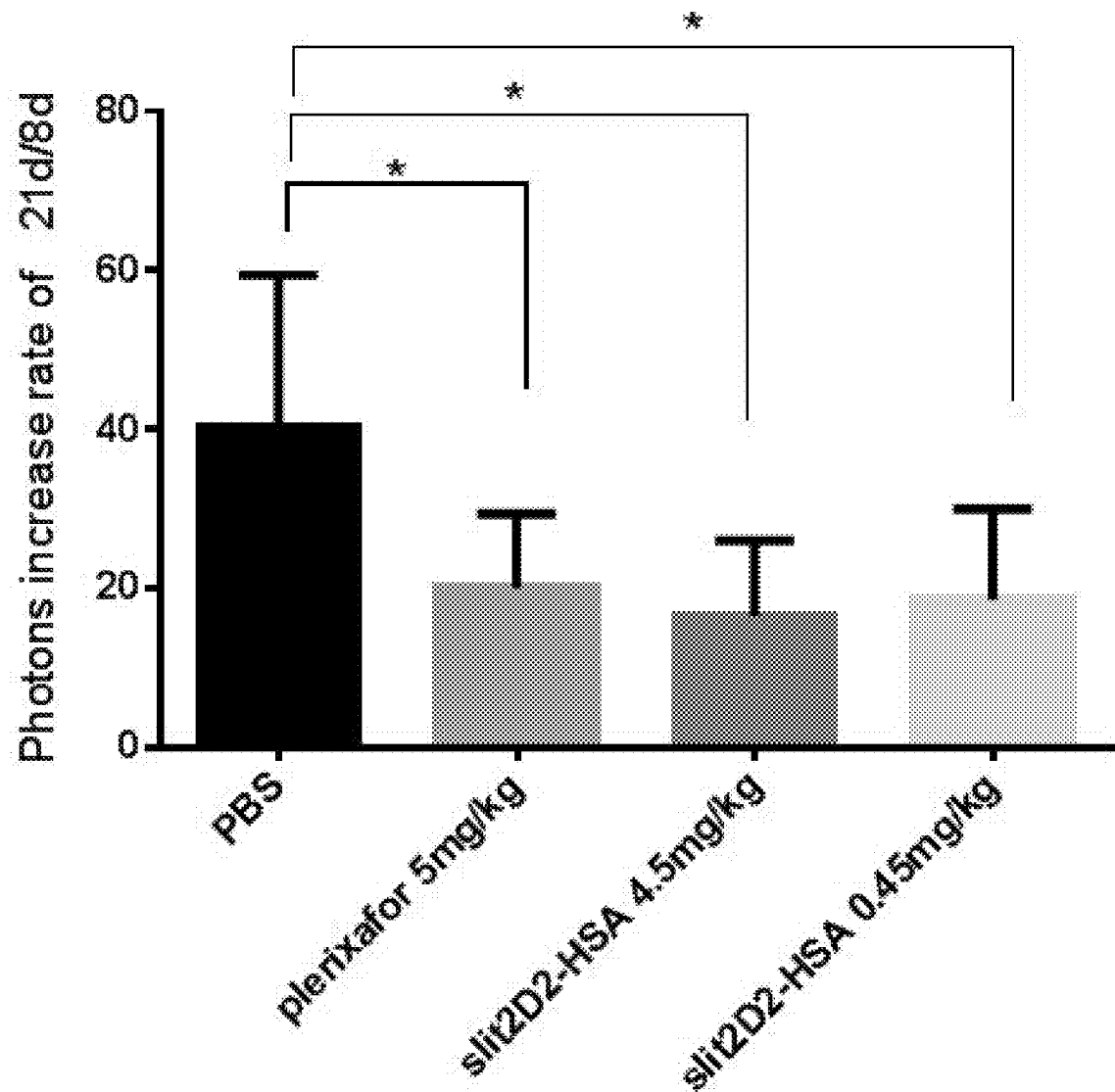
FIG. 13 shows a pharmacodynamic study of the tail vein injection and metastasis model of human breast cancer MDA-MB-231-Luc. The results showed that Slit2D2-HSA protein can significantly inhibit lung metastasis of MDA-MB-231 cells in mice.

FIG. 13 showed a pharmacodynamic study on the metastatic model obtained from the tail vein injection of human breast cancer MDA-MB-231-Luc. The result shows that Slit2D2-HSA protein can significantly inhibit lung metastasis of MDA-MB-231 cells in mice.

Example 4 the Detection of Anti-Tumor Metastasis Effect of Drugs on BALB/c Nude Mice Model Transplanted In Situ with MDA-MB-231 Human Breast Cancer and Safety Evaluation Thereof Cell Culture: MDA-MB-231 cells were cultured in L-15 medium with 10% fetal bovine serum. MDA-MB-231 cells in exponential growth phase were collected to suitable concentrations for in situ tumor inoculation in nude mice.

Animal modeling and grouping: BALB/c nude mice, female, 4-5 weeks, 14-18 g, purchased from Shanghai Xi Purr-will Kay Experimental Animal Co., Ltd. There were 2 groups in total after grouping, each group of 10 mice. All experimental mice were fed in SPF animal houses and adapted to the environment in advance for a period of at least 7 days. The experimental mice were inoculated with $1×10^7$ MDA-MB-231 cells under the right mammary fat pad. The cells were resuspended in 1:1 of L-15 medium and matrigel (0.1 ml/mouse), and the growth of the tumor was observed regularly. Each group was administered randomly according to tumor size and body weight of mice when the tumor growth was up to average of ~150 mm³. After two weeks of administration, tumor tissue was surgically removed and the drugs were administered for another six weeks. Detailed administration method, administration dose and administration route were shown in Table 1.

TABLE 2

Administration route, dose and program in animal models of MDA-MB-231

| group | n | administration group | dose (mg/kg) | volumn of administration | route of administration | frequency and period of administration |
|---|---|---|---|---|---|---|
| 1 | 10 | Vehicle control (PBS) | — | 10 ml/kg | i.p. | once every two days × 8 weeks |
| 2 | 10 | tested drug | 10 | 10 ml/kg | i.p. | once every two days × 8 weeks |
| 3 | 10 | tested drug | 5 | 10 ml/kg | i.p. | once every two days × 8 weeks |

Note:
n: number of animals; administration volumn: 10 ul/g;
i.p.: intraperitoneal injection.

The test drug in each group was diluted with PBS to a corresponding concentration for administration, and the diluted solution was stored at 4° C. until use.

Drugs were proteins, so the repeated freezing and thawing should be avoided.

Environmental conditions of laboratory animal breeding room: experimental animals were fed in the separate ventilation box with constant temperature and constant humidity, the temperature of breeding room was 20-26° C., the humidity was 30-70%. The box was ventilated for 10-20 times/hour. The light and dark alternate time between day and night was 12 h/12 h. Cobalt 60 radiation sterilized mouse full-price pellet feed was continuously supplied. The food intake was unlimited and free. The mice freely drank tap water (used after high-pressure steam sterilization) and water was supplied to the bottles without interruption. The feeding mouse box is a polysulfone box without pathogenic microorganisms; the bedding is corn cob. There were 5 animals in each box. The cage card was marked with the IACUC approval number, the experiment number, the start time for the experiment, the person in charge for the subject, the experimenter, the animal source, group and animal number, etc.; and the experimental animals were marked with earcuffs.

Aseptic operation: The entire process of the formulation for the compound solution, the administration, tumor measurement and weight weighing was performed in a biological safety cabinet or a clean bench.

Randomization: All animals were weighed before the administration and the tumor volume was measured with a vernier caliper. Since the volume of the tumor would affect the effectiveness of the treatment, a randomized grouping design was used to group the mice according to the tumor volume in mice to ensure similar tumor volumes across different groups.

Experimental observation and data collection: During the experiment, animal experiments were performed according to AAALAC requirements. After tumor inoculation, the common monitoring included the tumor growth and the effects of treatment on the normal behavior of animals, including activity of the laboratory animal, feeding and drinking, weight gain or loss, eye, hair and other abnormalities. Clinical symptoms observed during the experiment were recorded in the raw data. The weight and tumor size of the mice were measured twice a week throughout the experiment. The tumor size calculation formula: tumor volume (mm$^3$)=0.5×(long diameter of the tumor×short diameter of the tumor 2). At the end of the experiment, lung and lymphoid tissues were collected, H.E. staining was performed on the collected lung and lymphoid tissues, metastases in lung and lymphoid tissues were counted, and the number of metastatic animals was counted.

Experimental observation index and calculation:

1. Relative tumor inhibition rate TGI (%): TGI %=(1−T/C)×100%. T/C % is the relative tumor growth rate, which is the percentage of relative tumor volume or tumor weight of the treatment and control groups at a certain time point. T and C are the relative tumor volume (RTV) or tumor weight (TW) for the treatment group and the control group at a particular time point, respectively.

The calculation formula is as follows: T/C %=TRTV/CRTV×100% (TRTV: mean RTV of treatment group; CRTV: mean RTV of vehicle control group; RTV=Vt/V0, V0 is the tumor volume of the animal at the time of grouping, Vt is the tumor volume of the animal after the treatment), or T/C %=TTW/CTW×100% (TTW: mean tumor weight at the end of experiment in treatment group; CTW: average tumor weight at the end of the experiment in vehicle control group).

2. Tumor metastasis rate T/C (%): T/C %=T/C×100%. T/C % is the tumor metastasis rate, which is the percentage of the relative tumor metastasis rates of the treatment and the control groups at the end of the experiment. T and C are the number of tumor metastases in the lung and lymphoid tissues at the end of the experiment in the treatment and control groups, respectively.

The standards for the end of the experiment: During the experiment, feed, water intake and weight status in mice were closely observed. Mouse would be euthanized when the following criteria were met:

When the average tumor volume in a group of animals exceeded 3000 mm3, or before the animals were dying, the entire group of animals was euthanized.

Mouse would be euthanized when it lost ≥20% body weight for more than 72 hours.

Mouse would be euthanized if it had other health problems such as persistent loose stools, difficulty in breathing, bow back, or inability to properly intake the feed and drink.

When the mean tumor volume in the control group exceeded 2000 mm3 or one week after the last administration, the experiment would be terminated.

Statistical treatment: All experimental results were expressed as mean tumor volume±SE (standard error). One way ANOVA test method was used to compare the tumor volume, tumor weight and lung tumor metastasis rate of the treatment group with the control group, and the presence of significant difference was observed. All data were analyzed using SPSS 18.0. $p<0.05$ indicates a significant difference.

Figure 14A:
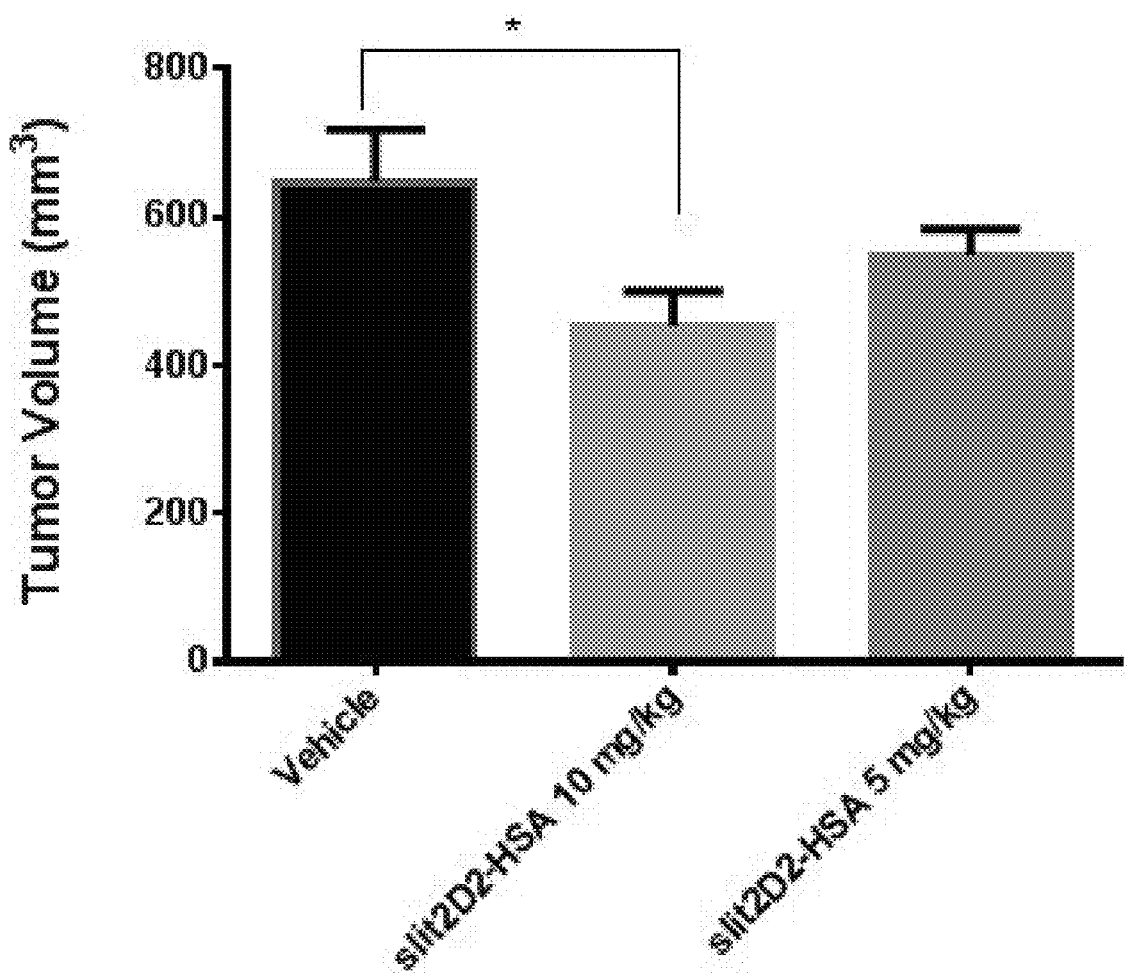
FIGS. 14A-14F show an anti-metastatic effect and safety evaluation of the drug in an animal model of BALB/c nude mice in situ implanted with MDA-MB-231 human breast cancer.
Figure 14B:
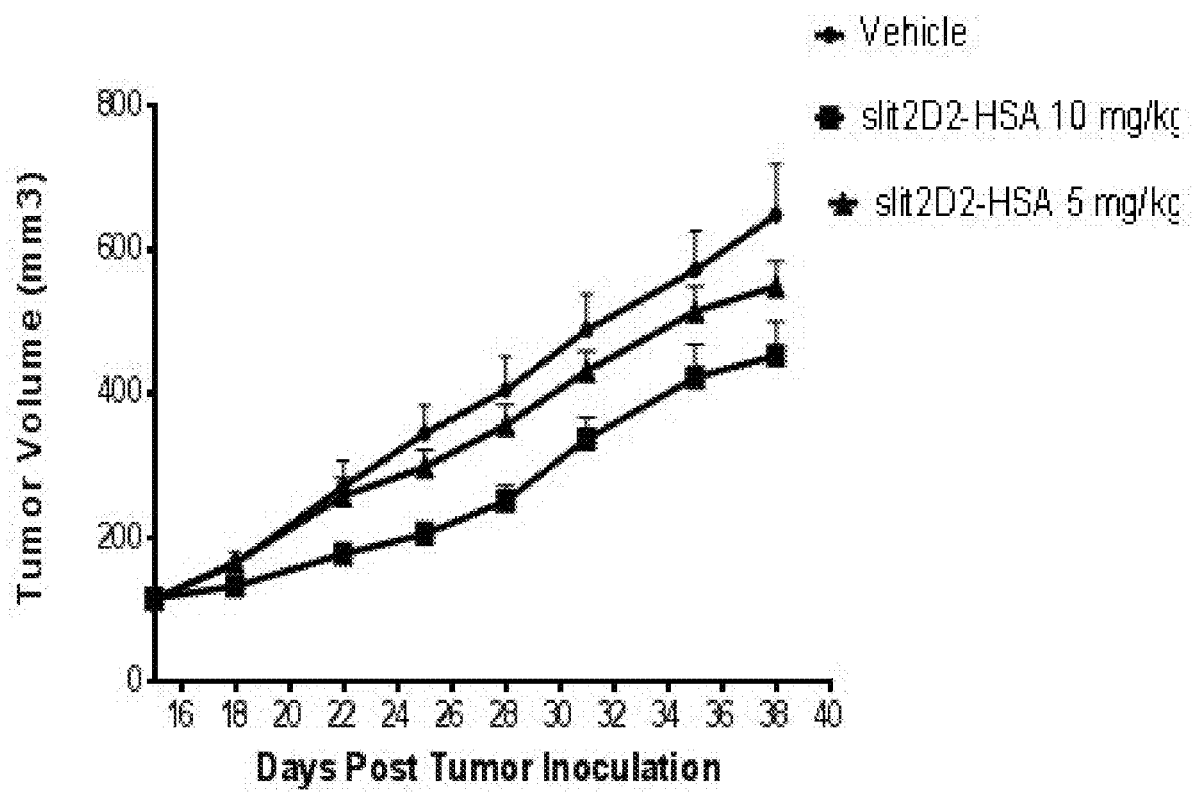
Figure 14C:
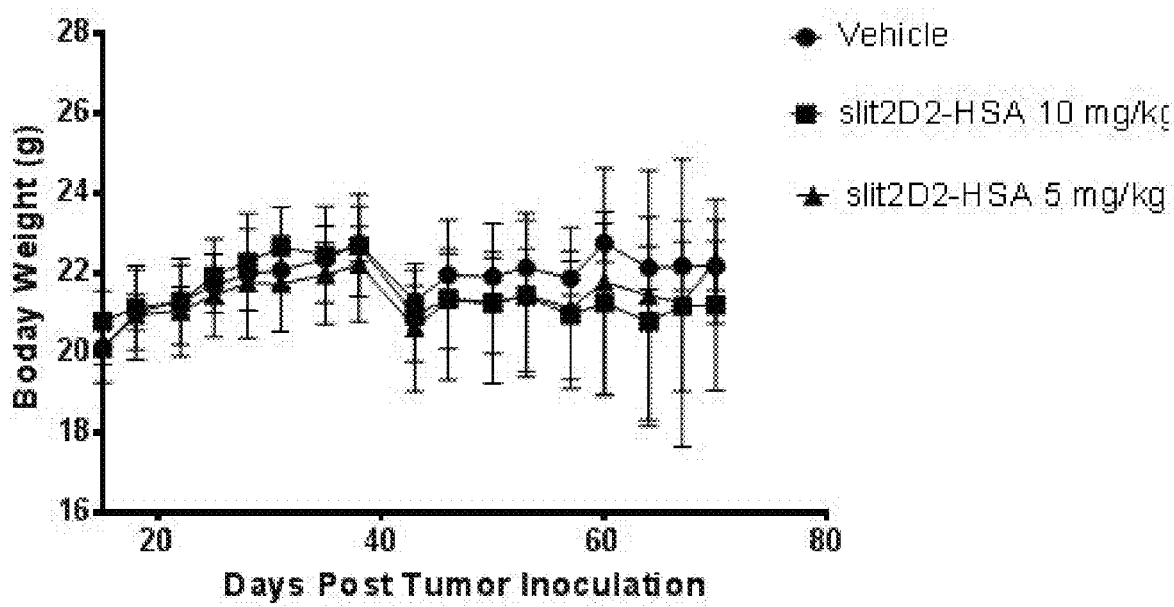
Figures 14D, 14E:
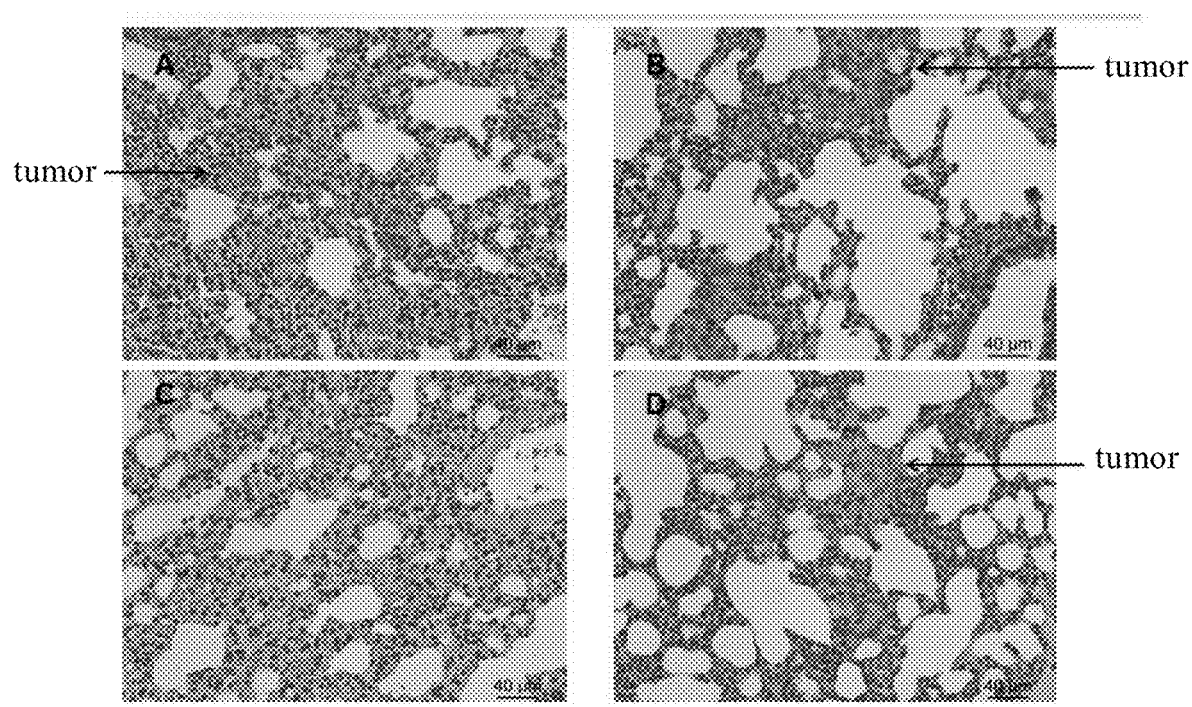
Figure 14F:
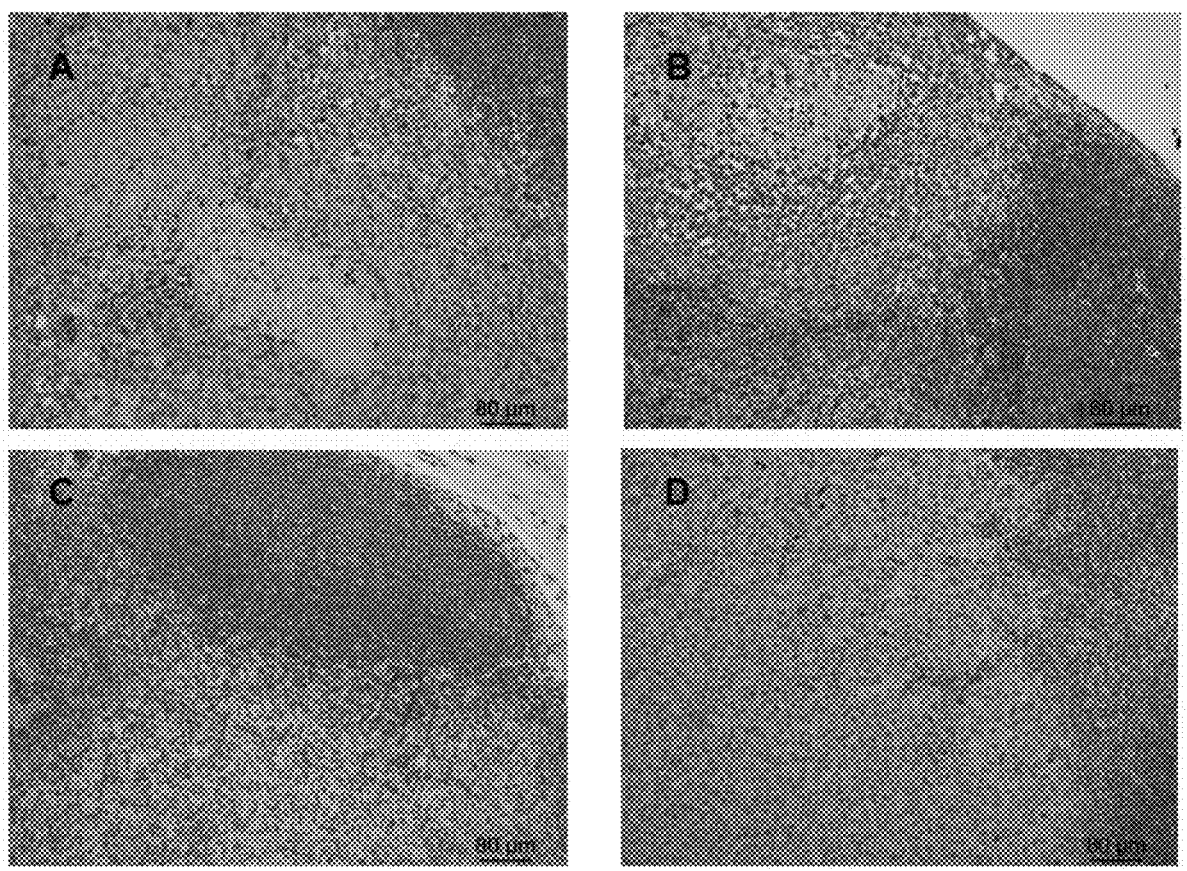

FIG. 14A-14F show the anti-metastatic effect and safety evaluation of the drug in BALB/c nude mice model in situ transplanted with human breast cancer MDA-MB -231. FIG. 14A shows the tumor volume of mice in different experiment groups, showing that the tumor volume of the experiment group of the fusion protein is significantly smaller than that of the vehicle control group; FIG. 14B shows the growth curve of the tumor, the tumor growth rate in the experiment group of the fusion protein is significantly lower than that in the vehicle control group; FIG. 14C shows the body weight changes of the mice in each experiment group after inoculation of the tumor. There was no significant difference between the control group and the experiment group, indicating that the fusion protein of the present invention had no obvious toxic and side effects. FIG. 14D shows inhibitory effect of the drug on tumor cell metastasis in the metastasis evaluation model established by surgical excision of the tumor that after each experiment group was inoculated with tumor cells and grew to a certain stage. FIG. 14E shows H&E staining of lung metastasis of the tumor. FIG. 14F (A was Control, B was 1 mg/kg of Slit2D2-HSA, C was 5 mg/kg of Slit2D2-HSA, and D was 10 mg/kg of Slit2D2-HAS) shows H & E staining for the tumor lymph node metastasis. The above results shows that the Slit2D2 -HSA protein can inhibit the growth of MDA-MB-231 cells to a certain extent at the dose of 10 mg/kg with the inhibition rate of 33.4%. In addition, the fusion protein of the present invention has an inhibitory effect on lung metastasis and lymph node metastasis of MDA-MB-231 cells in mice, wherein the effect of 5 mg/kg of the administration was better than that of 10 mg/kg of the administration. The positive metastasis rate was 66.7% at the dose of 5 mg/kg, compared with 90% metastasis rate in the control group, wherein the ratio of lymph node metastasis>10% was only 22%, compared with 50% for the control group, indicating that the drug had a good activity of inhibiting tumor metastasis. There was no significant difference in the body weight of the administration group and the control group, indicating that the drug had no obvious toxic and side effects.

All literatures mentioned in the present application are incorporated by reference herein, as though individually incorporated by reference. Additionally, it should be understood that after reading the above teachings, many variations and modifications may be made by the skilled in the art, and these equivalents also fall within the scope as defined by the appended claims.

REFERENCES

Wang, B., Y Xiao, B. B. Ding, N. Zhang, X. Yuan, L. Gui, K. X. Qian, S. Duan, Z. Chen, Y Rao and J. G Geng (2003). "Induction of tumor angiogenesis by Slit-Robo signaling and inhibition of cancer growth by blocking Robo activity." *Cancer Cell* 4(1): 19-29.

Wang, L. J., Y Zhao, B. Han, Y. G Ma, J. Zhang, D. M. Yang, J. W. Mao, F. T. Tang, W. D. Li, Y. Yang, R. Wang and J. G Geng (2008). "Targeting Slit-Roundabout signaling inhibits tumor angiogenesis in chemical-induced squamous cell carcinogenesis." *Cancer Sci* 99(3): 510-517.

Hohenester, E. (2008). "Structural insight into Slit-Robo signalling." *Biochem Soc Trans* 36(Pt 2): 251-256.

Morlot, C., W. Hemrika, R. A. Romijn, P. Gros, S. Cusack and A. A. McCarthy (2007). "Production of Slit2 LRR domains in mammalian cells for structural studies and the structure of human Slit2 domain 3." *Acta Crystallogr D Biol Crystallogr* 63(Pt 9): 961-968.

Seiradake, E., A. C. von Philipsborn, M. Henry, M. Fritz, H. Lortat-Jacob, M. Jamin, W. Hemrika, M. Bastmeyer, S. Cusack and A. A. McCarthy (2009). "Structure and functional relevance of the Slit2 homodimerization domain." *EMBO Rep* 10(7): 736-741.

The invention claimed is:

1. A fusion protein consisting of a polypeptide having the amino acid sequence as shown in SEQ ID NO: 3, wherein the fusion protein has a high activity in inhibiting tumor cell migration, invasion, and growth.

2. An isolated polynucleotide encoding the fusion protein of claim 1.

3. A pharmaceutical composition comprising:
the fusion protein of claim 1, and
a pharmaceutically acceptable carrier.

4. A method for treating a tumor comprising a step of administering a therapeutically effective amount of the fusion protein of claim 1 to a subject in need thereof.

5. The method of claim 4, wherein the tumor is selected from the group consisting of breast cancer, lung cancer, colorectal cancer, pancreatic cancer, ovarian cancer, prostate cancer, renal carcinoma, liver cancer, cerebral cancer, melanoma, multiple myeloma, chronic myeloid leukemia, and lymphoma.

* * * * *

SEQUENCE LISTING

```
<160> NUMBER OF SEQ ID NOS: 8

<210> SEQ ID NO 1
<211> LENGTH: 209
<212> TYPE: PRT
<213> ORGANISM: Homo sapiens
<220> FEATURE:
<223> OTHER INFORMATION: Slit2D2 protein element

<400> SEQUENCE: 1

Leu His Cys Pro Ala Ala Cys Thr Cys Ser Asn Asn Ile Val Asp Cys
1               5                   10                  15

Arg Gly Lys Gly Leu Thr Glu Ile Pro Thr Asn Leu Pro Glu Thr Ile
            20                  25                  30

Thr Glu Ile Arg Leu Glu Gln Asn Thr Ile Lys Val Ile Pro Pro Gly
        35                  40                  45

Ala Phe Ser Pro Tyr Lys Lys Leu Arg Arg Ile Asp Leu Ser Asn Asn
    50                  55                  60

Gln Ile Ser Glu Leu Ala Pro Asp Ala Phe Gln Gly Leu Arg Ser Leu
65                  70                  75                  80

Asn Ser Leu Val Leu Tyr Gly Asn Lys Ile Thr Glu Leu Pro Lys Ser
                85                  90                  95

Leu Phe Glu Gly Leu Phe Ser Leu Gln Leu Leu Leu Leu Asn Ala Asn
            100                 105                 110

Lys Ile Asn Cys Leu Arg Val Asp Ala Phe Gln Asp Leu His Asn Leu
```

```
                115                 120                 125
Asn Leu Leu Ser Leu Tyr Asp Asn Lys Leu Gln Thr Ile Ala Lys Gly
        130                 135                 140
Thr Phe Ser Pro Leu Arg Ala Ile Gln Thr Met His Leu Ala Gln Asn
145                 150                 155                 160
Pro Phe Ile Cys Asp Cys His Leu Lys Trp Leu Ala Asp Tyr Leu His
                165                 170                 175
Thr Asn Pro Ile Glu Thr Ser Gly Ala Arg Cys Thr Ser Pro Arg Arg
        180                 185                 190
Leu Ala Asn Lys Arg Ile Gly Gln Ile Lys Ser Lys Lys Phe Arg Cys
                195                 200                 205
Ser

<210> SEQ ID NO 2
<211> LENGTH: 585
<212> TYPE: PRT
<213> ORGANISM: Homo sapiens
<220> FEATURE:
<223> OTHER INFORMATION: HSA protein element

<400> SEQUENCE: 2

Asp Ala His Lys Ser Glu Val Ala His Arg Phe Lys Asp Leu Gly Glu
1               5                   10                  15
Glu Asn Phe Lys Ala Leu Val Leu Ile Ala Phe Ala Gln Tyr Leu Gln
                20                  25                  30
Gln Cys Pro Phe Glu Asp His Val Lys Leu Val Asn Glu Val Thr Glu
            35                  40                  45
Phe Ala Lys Thr Cys Val Ala Asp Glu Ser Ala Glu Asn Cys Asp Lys
        50                  55                  60
Ser Leu His Thr Leu Phe Gly Asp Lys Leu Cys Thr Val Ala Thr Leu
65                  70                  75                  80
Arg Glu Thr Tyr Gly Glu Met Ala Asp Cys Cys Ala Lys Gln Glu Pro
                85                  90                  95
Glu Arg Asn Glu Cys Phe Leu Gln His Lys Asp Asp Asn Pro Asn Leu
            100                 105                 110
Pro Arg Leu Val Arg Pro Glu Val Asp Val Met Cys Thr Ala Phe His
        115                 120                 125
Asp Asn Glu Glu Thr Phe Leu Lys Lys Tyr Leu Tyr Glu Ile Ala Arg
        130                 135                 140
Arg His Pro Tyr Phe Tyr Ala Pro Glu Leu Leu Phe Phe Ala Lys Arg
145                 150                 155                 160
Tyr Lys Ala Ala Phe Thr Glu Cys Cys Gln Ala Ala Asp Lys Ala Ala
                165                 170                 175
Cys Leu Leu Pro Lys Leu Asp Glu Leu Arg Asp Glu Gly Lys Ala Ser
            180                 185                 190
Ser Ala Lys Gln Arg Leu Lys Cys Ala Ser Leu Gln Lys Phe Gly Glu
        195                 200                 205
Arg Ala Phe Lys Ala Trp Ala Val Ala Arg Leu Ser Gln Arg Phe Pro
210                 215                 220
Lys Ala Glu Phe Ala Glu Val Ser Lys Leu Val Thr Asp Leu Thr Lys
225                 230                 235                 240
Val His Thr Glu Cys Cys His Gly Asp Leu Leu Glu Cys Ala Asp Asp
                245                 250                 255
Arg Ala Asp Leu Ala Lys Tyr Ile Cys Glu Asn Gln Asp Ser Ile Ser
            260                 265                 270
```

```
Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Arg Leu Ala Lys Thr
                340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
    435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
    515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 3
<211> LENGTH: 794
<212> TYPE: PRT
<213> ORGANISM: Artificial sequence
<220> FEATURE:
<223> OTHER INFORMATION: SlitD2-HSA fusion protein

<400> SEQUENCE: 3

Leu His Cys Pro Ala Ala Cys Thr Cys Ser Asn Asn Ile Val Asp Cys
1               5                   10                  15

Arg Gly Lys Gly Leu Thr Glu Ile Pro Thr Asn Leu Pro Glu Thr Ile
                20                  25                  30

Thr Glu Ile Arg Leu Glu Gln Asn Thr Ile Lys Val Ile Pro Pro Gly
            35                  40                  45
```

```
Ala Phe Ser Pro Tyr Lys Lys Leu Arg Arg Ile Asp Leu Ser Asn Asn
 50                  55                  60

Gln Ile Ser Glu Leu Ala Pro Asp Ala Phe Gln Gly Leu Arg Ser Leu
 65                  70                  75                  80

Asn Ser Leu Val Leu Tyr Gly Asn Lys Ile Thr Glu Leu Pro Lys Ser
                 85                  90                  95

Leu Phe Glu Gly Leu Phe Ser Leu Gln Leu Leu Leu Asn Ala Asn
            100                 105                 110

Lys Ile Asn Cys Leu Arg Val Asp Ala Phe Gln Asp Leu His Asn Leu
        115                 120                 125

Asn Leu Leu Ser Leu Tyr Asp Asn Lys Leu Gln Thr Ile Ala Lys Gly
    130                 135                 140

Thr Phe Ser Pro Leu Arg Ala Ile Gln Thr Met His Leu Ala Gln Asn
145                 150                 155                 160

Pro Phe Ile Cys Asp Cys His Leu Lys Trp Leu Ala Asp Tyr Leu His
                165                 170                 175

Thr Asn Pro Ile Glu Thr Ser Gly Ala Arg Cys Thr Ser Pro Arg Arg
                180                 185                 190

Leu Ala Asn Lys Arg Ile Gly Gln Ile Lys Ser Lys Phe Arg Cys
            195                 200                 205

Ser Asp Ala His Lys Ser Glu Val Ala His Arg Phe Lys Asp Leu Gly
210                 215                 220

Glu Glu Asn Phe Lys Ala Leu Val Leu Ile Ala Phe Ala Gln Tyr Leu
225                 230                 235                 240

Gln Gln Cys Pro Phe Glu Asp His Val Lys Leu Val Asn Glu Val Thr
                245                 250                 255

Glu Phe Ala Lys Thr Cys Val Ala Asp Glu Ser Ala Glu Asn Cys Asp
                260                 265                 270

Lys Ser Leu His Thr Leu Phe Gly Asp Lys Leu Cys Thr Val Ala Thr
            275                 280                 285

Leu Arg Glu Thr Tyr Gly Glu Met Ala Asp Cys Cys Ala Lys Gln Glu
    290                 295                 300

Pro Glu Arg Asn Glu Cys Phe Leu Gln His Lys Asp Asp Asn Pro Asn
305                 310                 315                 320

Leu Pro Arg Leu Val Arg Pro Glu Val Asp Val Met Cys Thr Ala Phe
                325                 330                 335

His Asp Asn Glu Glu Thr Phe Leu Lys Lys Tyr Leu Tyr Glu Ile Ala
            340                 345                 350

Arg Arg His Pro Tyr Phe Tyr Ala Pro Glu Leu Leu Phe Phe Ala Lys
    355                 360                 365

Arg Tyr Lys Ala Ala Phe Thr Glu Cys Cys Gln Ala Ala Asp Lys Ala
370                 375                 380

Ala Cys Leu Leu Pro Lys Leu Asp Glu Leu Arg Asp Glu Gly Lys Ala
385                 390                 395                 400

Ser Ser Ala Lys Gln Arg Leu Lys Cys Ala Ser Leu Gln Lys Phe Gly
                405                 410                 415

Glu Arg Ala Phe Lys Ala Trp Ala Val Ala Arg Leu Ser Gln Arg Phe
            420                 425                 430

Pro Lys Ala Glu Phe Ala Glu Val Ser Lys Leu Val Thr Asp Leu Thr
    435                 440                 445

Lys Val His Thr Glu Cys Cys His Gly Asp Leu Leu Glu Cys Ala Asp
    450                 455                 460
```

Asp Arg Ala Asp Leu Ala Lys Tyr Ile Cys Glu Asn Gln Asp Ser Ile
465                 470                 475                 480

Ser Ser Lys Leu Lys Glu Cys Cys Glu Lys Pro Leu Leu Glu Lys Ser
            485                 490                 495

His Cys Ile Ala Glu Val Glu Asn Asp Glu Met Pro Ala Asp Leu Pro
        500                 505                 510

Ser Leu Ala Ala Asp Phe Val Glu Ser Lys Asp Val Cys Lys Asn Tyr
    515                 520                 525

Ala Glu Ala Lys Asp Val Phe Leu Gly Met Phe Leu Tyr Glu Tyr Ala
    530                 535                 540

Arg Arg His Pro Asp Tyr Ser Val Val Leu Leu Leu Arg Leu Ala Lys
545                 550                 555                 560

Thr Tyr Glu Thr Thr Leu Glu Lys Cys Cys Ala Ala Ala Asp Pro His
            565                 570                 575

Glu Cys Tyr Ala Lys Val Phe Asp Glu Phe Lys Pro Leu Val Glu Glu
        580                 585                 590

Pro Gln Asn Leu Ile Lys Gln Asn Cys Glu Leu Phe Glu Gln Leu Gly
    595                 600                 605

Glu Tyr Lys Phe Gln Asn Ala Leu Leu Val Arg Tyr Thr Lys Lys Val
    610                 615                 620

Pro Gln Val Ser Thr Pro Thr Leu Val Glu Val Ser Arg Asn Leu Gly
625                 630                 635                 640

Lys Val Gly Ser Lys Cys Cys Lys His Pro Glu Ala Lys Arg Met Pro
            645                 650                 655

Cys Ala Glu Asp Tyr Leu Ser Val Val Leu Asn Gln Leu Cys Val Leu
        660                 665                 670

His Glu Lys Thr Pro Val Ser Asp Arg Val Thr Lys Cys Cys Thr Glu
        675                 680                 685

Ser Leu Val Asn Arg Arg Pro Cys Phe Ser Ala Leu Glu Val Asp Glu
    690                 695                 700

Thr Tyr Val Pro Lys Glu Phe Asn Ala Glu Thr Phe Thr Phe His Ala
705                 710                 715                 720

Asp Ile Cys Thr Leu Ser Glu Lys Glu Arg Gln Ile Lys Lys Gln Thr
            725                 730                 735

Ala Leu Val Glu Leu Val Lys His Lys Pro Lys Ala Thr Lys Glu Gln
        740                 745                 750

Leu Lys Ala Val Met Asp Asp Phe Ala Ala Phe Val Glu Lys Cys Cys
    755                 760                 765

Lys Ala Asp Asp Lys Glu Thr Cys Phe Ala Glu Glu Gly Lys Lys Leu
    770                 775                 780

Val Ala Ala Ser Gln Ala Ala Leu Gly Leu
785                 790

<210> SEQ ID NO 4
<211> LENGTH: 2399
<212> TYPE: DNA
<213> ORGANISM: Artificial sequence
<220> FEATURE:
<223> OTHER INFORMATION: Encoding DNA sequence of SlitD2-HSA fusion
      protein

<400> SEQUENCE: 4
ctctggctcc ccggggcgcg ctgtttgcac tgccctgccg cctgtacctg tagcaacaat    60
atcgtagact gtcgtgggaa aggtctcact gagatcccca caaatcttcc agagaccatc   120
acagaaatac gtttggaaca gaacacaatc aaagtcatcc ctcctggagc tttctcacca   180

-continued

```
tataaaaagc ttagacgaat tgacctgagc aataaagatc tctgaacttg caccagatgc        240
tttccaagga ctacgctctc tgaattcact tgtcctctat ggaaataaaa tcacagaact        300
ccccaaaagt ttatttgaag gactgttttc cttacagctc catattgaat gccaacaaga        360
taaactgcct tcgggtagat gcttttcagg atctccacaa cttgaacctt ctctccctat        420
atgacaacaa gcttcagacc atcgccaagg ggacctttc acctcttggc cattcaaact        480
atgcatttgg cccagaaccc ctttatttgt gactgccatc tcaagtggct agcggattat        540
ctccatacca acccgattga ccagtggt gcccgttgca ccagccccg ccgctgcaaa         600 caaaagaatt ggacagatca aaagcaagaa attccgttgt tcagatgcac acaagagtga        660
ggttgctcat cggtttaaag atttgggaga agaaaattc aaagccttgg tgttgattgc         720
tttgctcagt atcttagcag tgtccatttg aagatcatgt aaaattagtg aatgaagtaa        780
ctgaatttgc aaaaacatgt gttgctgatg agtcagctga aaattgtgac aaatcacttc        840
ataccttttt ggagacaaat tagcacagtt gcaactcttc gtgaaaccta tggtgaaatg        900
gctgactgct gtgcaaaaca agaacctgag agaaatgaat gcttcttgca acacaaagat        960
gacaacccaa actcccccga ttggtgagac agaggttgat gtgatgtgca ctgcttttca       1020
tgacaatgaa gagacatttt tgaaaaaata cttatatgaa attgccagaa gacatcctta       1080
cttttatgcc ccggaaccct tttctttgct aaaaggataa agctgctttt acagaatgtt       1140
gccaagctgc tgataaagct gcctgcctgt tgccaaagct cgatgaactt cgggatgaag       1200
ggaaggcttc gtctgccaaa caggactcaa gtgtgccagt ctcaaaaatt tggagaaaga       1260
gctttcaaag catgggcagt agctcgcctg agccagagat ttcccaaagc tgagtttgca       1320
gaagtttcca agttagtgac agatcttaca aagtccacac ggaatgctgc atggagatct       1380
gcttgaatgt gctgatgaca gggcggacct tgccaagtat atctgtgaaa atcaagattc       1440
gatctccagt aaactgaagg aatgctgtga aaaactctgt tggaaaaatc ccactgcttg       1500
ccgaagtgga aaatgatgag atgcctgctg acttgccttc attagctgct gattttgttg       1560
aaagtaagga tgtttgcaaa aactatgctg aggcaaagga ttcttcctgg gcatgttttt       1620
gtataatatg caagaaggca tcctgattac tctgtcgtgc tgctgctgag acttgccaag       1680
acatatgaaa ccactctaga gaagtgctgt gccgctgcag atcctcagaa tgctatgcca       1740
aagtgttcga taatttaaac ctcttgtgga agagcctcag aatttaatca acaaaattg       1800 tgagcttttt gagcagcttg gagagtacaa attccagaat gcgctattag ttcttacacc       1860
aagaaagtac cccaagtgca actccaactc ttgtagaggt ctcaagaaac ctaggaaaag       1920
tgggcagcaa atgttgtaaa catcctgaag caaaagaat gccctgtgca gaagactatt        1980
atccgtggtc ctgaaccagt tatgttgttg catgagaaaa cgccagtaag tgacagagtc       2040
accaaatgct gcacagaatc cttggtgaac aggcgaccat gcttttcagc tctggaagtc       2100
gatgaacata cgttcccaaa gagtttaatg ctaaacattc accttccatg cagatatatg       2160
cacactttct gagaaggaga gacaaatcaa gaaacaaact gcacttgttg agctcgtgaa       2220
acacaagccc aggcaacaaa agagcaactg aaagctgttt ggatgatttc gcagcttttg       2280
tagagaagtg ctgcaaggct gacgataagg agacctgctt tgccgaggag ggtaaaaaac       2340
ttgttgctgc aagtcaactg ccttaggctt ataagaattc attgatcatt aatcagcca       2399
```

<210> SEQ ID NO 5
<211> LENGTH: 48
<212> TYPE: DNA

```
<213> ORGANISM: Artificial sequence
<220> FEATURE:
<223> OTHER INFORMATION: primer

<400> SEQUENCE: 5
ctctggctcc ccggggcgcg ctgtttgcac tgccctgccg cctgtacc                48

<210> SEQ ID NO 6
<211> LENGTH: 45
<212> TYPE: DNA
<213> ORGANISM: Artificial sequence
<220> FEATURE:
<223> OTHER INFORMATION: primer

<400> SEQUENCE: 6
gcaacctcac tcttgtgtgc atctgaacaa cggaatttct tgctt                   45

<210> SEQ ID NO 7
<211> LENGTH: 23
<212> TYPE: DNA
<213> ORGANISM: Artificial sequence
<220> FEATURE:
<223> OTHER INFORMATION: primer

<400> SEQUENCE: 7
gatgcacaca agagtgaggt tgc                                           23

<210> SEQ ID NO 8
<211> LENGTH: 46
<212> TYPE: DNA
<213> ORGANISM: Artificial sequence
<220> FEATURE:
<223> OTHER INFORMATION: primer

<400> SEQUENCE: 8
tggctgatta atgatcaatg aattcttata agcctaaggc agcttg                  46
```